United States Patent
Glinka et al.

(10) Patent No.: US 8,084,643 B2
(45) Date of Patent: *Dec. 27, 2011

(54) WATER-SOLUBLE PRODRUGS OF FLORFENICOL AND ITS ANALOGS

(75) Inventors: Tomasz W. Glinka, Cupertino, CA (US); Jason Z. Zhang, Foster City, CA (US)

(73) Assignee: Intervet Inc., Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/953,962

(22) Filed: Dec. 11, 2007

(65) Prior Publication Data

US 2008/0188556 A1    Aug. 7, 2008

Related U.S. Application Data

(60) Provisional application No. 60/874,864, filed on Dec. 13, 2006.

(51) Int. Cl.
    A61K 31/21    (2006.01)
    C07C 233/00   (2006.01)

(52) U.S. Cl. ........................ 564/209; 514/506

(58) Field of Classification Search .................. 564/182
    See application file for complete search history.

(56) References Cited

U.S. PATENT DOCUMENTS

| | | |
|---|---|---|
| 2,776,992 A | 1/1957 | Gregory |
| 3,100,781 A | 8/1963 | Concilio et al. |
| 3,183,265 A | 5/1965 | von Strandtmann et al. |
| 3,294,818 A | 12/1966 | Bobowski et al. |
| 3,405,165 A | 10/1968 | Rebstock et al. |
| 3,475,470 A | 10/1969 | Rebstock et al. |
| 3,740,411 A | 6/1973 | Akiyama et al. |
| 3,770,889 A | 11/1973 | Gutschick et al. |
| 3,950,360 A | 4/1976 | Aoki et al. |
| 3,984,564 A | 10/1976 | Aoki et al. |
| 4,199,569 A | 4/1980 | Chabala et al. |
| 4,235,892 A | 11/1980 | Nagabhushan |
| 4,310,519 A | 1/1982 | Albers-Schonberg et al. |
| 4,311,857 A | 1/1982 | Nagabhushan |
| 4,361,557 A | 11/1982 | Nagabhushan |
| 4,582,918 A | 4/1986 | Nagabhushan et al. |
| 4,743,700 A | 5/1988 | Jommi et al. |
| 4,820,695 A | 4/1989 | Debono et al. |
| 4,876,352 A | 10/1989 | Schumacher et al. |
| 4,916,154 A | 4/1990 | Asato et al. |
| 4,918,095 A | 4/1990 | Della Bella et al. |
| 4,973,750 A | 11/1990 | Nagabhushan et al. |
| 5,082,863 A | 1/1992 | Apelian et al. |
| 5,089,480 A | 2/1992 | Gibson et al. |
| 5,105,009 A | 4/1992 | Jommi et al. |
| 5,153,328 A | 10/1992 | Jommi et al. |
| 5,227,494 A | 7/1993 | Schumacher et al. |
| 5,243,056 A | 9/1993 | Jommi et al. |
| 5,288,710 A | 2/1994 | Cvetovich |
| 5,332,835 A | 7/1994 | Jommi et al. |
| 5,352,832 A | 10/1994 | Wu et al. |
| 5,382,673 A | 1/1995 | Clark et al. |
| 5,399,717 A | 3/1995 | Cvetovich et al. |
| 5,567,844 A | 10/1996 | Jommi et al. |
| 5,621,111 A | 4/1997 | Lui et al. |
| 5,663,361 A | 9/1997 | Towson et al. |
| 5,789,599 A | 8/1998 | Davis et al. |
| 5,908,937 A | 6/1999 | Jommi et al. |
| 5,958,888 A | 9/1999 | Macy et al. |
| 6,054,434 A | 4/2000 | Kropp et al. |
| 6,239,112 B1 | 5/2001 | Macy et al. |
| 6,270,768 B1 | 8/2001 | O'Connell et al. |
| 6,271,255 B1 | 8/2001 | Leadlay et al. |
| 6,339,063 B1 | 1/2002 | Kropp et al. |
| 6,437,151 B2 | 8/2002 | Leadlay et al. |
| 6,472,371 B1 | 10/2002 | Dirlam et al. |
| 6,514,492 B1 | 2/2003 | Gao et al. |
| 6,514,945 B1 | 2/2003 | Boettner |
| 6,790,867 B2 | 9/2004 | Kohan et al. |
| 6,825,327 B2 | 11/2004 | Sklavounos et al. |
| 7,041,670 B2 | 5/2006 | Boojamra et al. |
| 7,153,842 B2 | 12/2006 | Hecker et al. |
| 7,361,689 B2 | 4/2008 | Shuster et al. |
| 7,439,268 B2 | 10/2008 | Murthy et al. |
| 2003/0065939 A1 | 4/2003 | Nosaka |

(Continued)

FOREIGN PATENT DOCUMENTS

BE    638 755 A    4/1964

(Continued)

OTHER PUBLICATIONS

Hcaplus 1981:139433 (1981).*
Hcaplus 1981:139433 (1981), "1-Aryl-2-acylamido-3-fluoro-1-propanols and pharmaceuticals compositions containing them", Nagabhushan, Tattanahalli.*
Banerjee, Anamitro et al., "Photoreleasable protecting groups based on electron transfer chemistry. Donor sensitized release of phenacyl groups from alcohols, phosphates and diacids," *Tetrahedron*, 55(44): 12699-12710 (1999).
Bolhofer, William, "The Preparation of Hydroxyphenylserines from benzyloxybenzaldehydes and Glycine," *J. Am. Chem. Soc.* 76:1322-26(1954).
Bolton, Lance F. et al., "Detection of multidrug-resistant *Salmonella enterica* serotype typhimurium DT104 based on a gene which confers cross-resistance to florfenicol and chloramphenicol," *J Clin Microbiol.* May 1999;37(5):1348-1351.

(Continued)

*Primary Examiner* — Janet Andres
*Assistant Examiner* — Heidi Reese
(74) *Attorney, Agent, or Firm* — David Kerwick

(57) ABSTRACT

The present invention discloses certain novel prodrugs of florfenicol and/or of florfenicol analogs, including prodrugs of salts pharmaceutically acceptable salts of florfenicol and its analogs, including nitrogen-containing esters of the secondary alcohol group of florfenicol and of its analogs, and pharmaceutically acceptable salts thereof, compositions containing them, and methods of administering them to subjects. In particular embodiments the prodrugs are sufficiently water-soluble to serve the functions needed of a water-soluble prodrug of florfenicol or of a water-soluble prodrug of a florfenicol analog. A certain subclass of the compounds also possesses the hydrolytic stability needed to maintain the prodrug in solution in the subject's system until appropriate conditions exist when the prodrug can hydrolyze, releasing florfenicol or the florfenicol analog in question.

23 Claims, No Drawings

U.S. PATENT DOCUMENTS

| | | | |
|---|---|---|---|
| 2004/0082553 | A1 | 4/2004 | Boojamra et al. |
| 2005/0014828 | A1 | 1/2005 | Murthy et al. |
| 2005/0182031 | A1 | 8/2005 | Hecker et al. |
| 2005/0182059 | A1 | 8/2005 | Winzenberg et al. |
| 2005/0182138 | A1 | 8/2005 | John et al. |
| 2005/0182139 | A1 | 8/2005 | Shuster et al. |
| 2006/0063841 | A1 | 3/2006 | Meyer et al. |
| 2006/0128779 | A1 | 6/2006 | Winzenberg et al. |
| 2006/0281695 | A1 | 12/2006 | Meyer et al. |
| 2007/0155799 | A1 | 7/2007 | Glinka et al. |
| 2007/0238700 | A1 | 10/2007 | Winzenberg et al. |
| 2008/0146640 | A1 | 6/2008 | Glinka |
| 2008/0153906 | A1* | 6/2008 | Celly et al. ............ 514/550 |

FOREIGN PATENT DOCUMENTS

| | | |
|---|---|---|
| BE | 669 982 A | 3/1966 |
| EP | 0 014 437 B1 | 8/1980 |
| FR | 4 604 M | 11/1966 |
| GB | 804986 | 11/1958 |
| GB | 1117616 | 6/1968 |
| GB | 1117617 | 6/1968 |
| GB | 1173562 | 12/1969 |
| GB | 1263116 | 2/1972 |
| WO | WO 03/077828 A2 | 9/2003 |
| WO | WO 2005/009429 A1 | 2/2005 |
| WO | WO 2008/066444 A1 | 6/2008 |
| WO | WO 2008/076256 A1 | 6/2008 |
| WO | WO 2008/076261 A2 | 6/2008 |

OTHER PUBLICATIONS

Von Dem Bruch, K. et al., "The 3-(3-pyridyl)allyloxycarbonyl (paloc) moiety—a stable, amino-protecting group for peptide syntheses in organic media and in water that is cleavable under neutral conditions," *Angew. Chem.* 29(12): 1457-1459 (1990).

Brunelle, Daniel, "Novel catalysis of o-nitrophenyl carbonates by p-dimethylaminonopyridine," *Tetrahedron Lett.* 23(17): 1739-1742 (1982).

Castro, Enrique A. et al., "Kinetic investigation of the phenolysis of phenyl 4-nitrophenyl and phenyl 2,4-dinitrophenyl carbonates," *J. Chem. Soc. Perkin. Trans.* 2(12):2351-2354 (2001).

Chen, C. et al., "Synthesis of (+)-CP-263,114" *J. Am. Chem. Soc.* 122 (30): 7424-7425 (2000).

Chmielewski, Marcin K. et al., "Thermolytic Carbonates for Potential 5'-Hydroxyl Protection of Deoxyribonucleosides," *J. Org. Chem.*, 68(26):10003-10012 (2003).

Cloeckaert, Axel et al., "Nonenzymatic chloramphenicol resistance mediated by IncC plasmid R55 is encoded by a floR gene variant," *Antimicrobial Agents and Chemotherapy* 45(8):2381-2 (2001).

Compendium of Veterinary Products, Seventh Edition, pp. 1841-1842, 2043 (2003).

Database CA [Online]; Chemical Abstracts Service, Columbus, Ohio, US; "1-(4-Methylsulfonylphenyl)-2-acetamido-3-fluoro-1-propanol derivatives for infection control in fish", Database accession No. 1984:577519; JP 59 112913A (1984) Abstract.

Diaz, Monica et al., "CAL-B-Catalyzed Alkoxycarbonylation of A-Ring Stereoisomeric Synthons of 1α,25-Dihydroxyvitamin $D_3$ and 1α,25-Dihydroxy-19-*nor*-previtamin $D_3$: A Comparative Study. First Regioselective Chemoenzymatic Synthesis of 19-*nor*-A-Ring Carbonates," *J. Org. Chem.* 66(12):4227-4232 (2001).

Dubowchik, Gene M. et al., "Cathepsin B-sensitive dipeptide prodrugs. 2. Models of anticancer drugs paclitaxel (Taxol®), mitomycin C and doxorubicin," *Bioorg. Med. Chem. Lett.* 8(23):3347-3352 (1998).

Evans, David D. et al., "Analogues of Chloramphnicol. Part III," *J. Chem. Soc.* 1687-90 (1954).

Fleisher, D. et al., "Improved oral drug delivery: solubility limitations overcome by the use of prodrugs", *Adv. Drug Delivery Rev.*, 19:115-130 (1996).

Grehn, Leif et al., "A Simple Method for tert-Butoxycarbonylation of Amides,"*Acta Chemica Scandinavica* B 40:745-750 (1986).

Greiner, Beate et al., "Nucleotides. Part LVII. Synthesis of phosphoramidite building blocks of 2-amino-2-deoxyribonucleosides: new compounds for oligonucleotide synthesis," *Helv. Chim. Acta* 81(8):1528-1544 (1998).

Hansch, Corwin, et al., "Structure-activity relationship of chloramphenicols," *J Med Chem.*, 16(8):917-22 (1973).

Harada et al., "Allyloxycarbonyl group as a protective group for the hydroxyl group in carbohydrates," *Journal of Carbohydrate Chemistry* 14(1):165-170 (1995).

Herbert, Richard B. et al., "Preparation of (2R,3S)-β-hydroxy-α-amino acids by use of a novel Streptomyces aldolase as a resolving agent for racemic material," *Can. J. Chem.* 72:114-17 (1994).

Hoflack, G. et al., "Efficacy of tilmicosin phosphate (Pulmotil premix) in feed for the treatment of a clinical outbreak of *Actinobacillus pleuropneumoniae* infection in growing finishing pigs," *J Vet Med B Infect Dis Vet Public Health* 48(9):655-64 (2001).

Iimori, Takamasa et al., "A novel intramolecular decarboxylative glycosylation via mixed carbonate," *Tetrahedron Lett.* 37(13):2267-2270 (1996).

Ishizuka, Tadao et al., "Mild and Selective Ring-Cleavage of Cyclic Carbamates to Amino Alcohols," *Tetrahedron Letters* 28:4185-88 (1987).

Jommi, Giancarlo et al., "2-Oxazolidinones as Regioselective Protection of β-Amino Alcohols in the Synthesis of 2-Amino-1-Aryl-3-Fluoro-1-Proponals," *Gazzetta Chimica Italiana* 116:485-89 (1986).

Jommi, Giancarlo et al., "Mild Recovery of β-amino Alcohols from the Corresponding 2-Oxazolidinones," *Gazzetta Chimica Italiana* 118:75-76 (1988).

Kenar, James A. et al., "Synthesis and characterization of dialkyl carbonates prepared from mid-, long-chain, and guerbet alcohols," *J. Am. Oil Chem. Soc.* 81(3):285-291 (2004).

Keyes, Kathleen et al., "Detection of florfenicol resistance genes in *Escherichia coli* isolated from sick chickens," *Antimicrob Agents Chemother.* 44(2):421-4 (2000).

Kim, Eun-Heui et al., "Sequence Analysis of the Florfenicol Resistance Gene Encoded in the Transferable R-Plasmid of a Fish Pathogen, *Pasteurella piscicida,*" *Microbiol. Immunol.* 40:665-69 (1996).

Kong, A. et al., "Disposition of methylprednisolone and its sodium succinate prodrug in vivo and in perfused liver of rats: nonlinear and sequential first-pass elimination", *J Pharm Sci*, 80(5):409-415 (1991).

Kozikowski, Alan P. et al., "Novel PI Analogues Selectively Block Activation of the Pro-survival Serine/Threonine Kinase Akt," *J. Am. Chem. Soc.*, 125 (5):1144-1145 (2003).

Kramer, WG et al., "Comparative bioavailability of intravenous and oral chloramphenicol in adults", *J. Clin Pharmacol* 24(4):181-186 (1984).

Kryczka, B., "Syntheses de carbonates et carbamates benzyliques et allyliques,"*Bull. Soc. Chim. Belg.* 101(2) :147-157 (1992).

Lal, Gauri S. et al., "Bis(2-methoxyethyl)aminosulfur Trifluoride: A New Broad-Spectrum Deoxofluorinating Agent with Enhanced Thermal Stability," *J. Org. Chem.* 64:7048-54 (1999).

Lam, Patrick Y.S. et al., "New Aryl/Heteroaryl C-N Bond Cross-coupling Reactions via Arylboronic Acid/Cupric Acetate Arylation," *Tetrahedron Letters* 39:2941-44 (1998).

Lam, Patrick Y.S. et al., "Copper Promoted Aryl/Saturated Heterocyclic C-N Bond Cross-Coupling with Arylboronic Acid and Arylstannane," *Synlett* 5 :674-76 (2000).

Lam, Patrick Y.S. et al., "Copper-catalyzed general C-N and C-O bond cross-coupling with arylboronic acid," *Tetrahedron Letters* 42:3415-18 (2001).

Li, Hong-Yu et al., "Synthesis of DNA Oligomers Possessing a Covalently Cross-Linked Watson-Crick Base Pair Model," *Angewandte Chemie International Edition* 40(8):1471-1475 (2001).

Marca, G. et al., "Observations on antibacterial activity of thiamphenicol glycinate acetylcysteinate", Database Caplus [online], Chemical Abstracts Service, Columbus, Ohio, US; XP002480575; database accession No. 1980:631596, Abstract (1979).

Marca, G. et al., "Osservazioni sull'attiviata antibatterica del tiamfenicolo glicinato acetilcisteinato", *Quaderni Sclavo di Diagnostica Clinica e di Laboratorio*, 15(Suppl 01):777-784 XP009018668 (1979).

Mindl et al., "Alkoxycarbonylation of alcohols and phenols by nitrosoformates," *Collect. Czech. Chem. Commun.* 61(7):1053-1063 (1996).

Mitscher, Lester A. et al., "Circular dichroism studies of aryl diasteroisomers. 3. Cupra A spectra of chloramphenicol derivatives," *J Med Chem.* 16(2):98-101 (1973).

Moris, Franciso et al., "Enzymatic acylation and alkoxycarbonylation of α-, xylo-, anhydro-, and arabino-nucleosides," *Tetrahedron* 49(44):10089-10098 (1993).

Moris, Franciso et al., "A novel and convenient route to 3'-carbonates from unprotected 2'-deoxynucleosides through an enzymic reaction," *J. Org. Chem.* 57(8): 2490-2492 (1992).

Morris et al., "Analogues of Chloramphenicol. Part I," *J. Chem. Soc.* 1680-86 (1954).

National Office of Animal Health, Antibiotics for Animal—An Overview, Briefing Document No. 6, 2004.

Nielsen, Peter E., et al., "Light Sensitive Chloramphenicol Analogues," *Acta Chemica Scandinavica* B 29:662-66 (1975).

Nongkunsarn, P. et al., "Rearrangement and radical mediated decarboxylation of trimethylsilyl benzoates using xenon difluoride", *J. Chem. Soc., Perking Trans. 1*, 2:121-122 (1996).

Olofson, R.A. et al., "A regiospecific and stereospecific route to enol carbonates and carbamates: closer look at a 'naked anion'", *Tetrahedron Lett.* 21:819-822 (1980).

PCT International Search Report dated Jun. 27, 2005 for PCT Application No. PCT/US2004/043199.

PCT International Search Report dated Jun. 28, 2005 for PCT Application No. PCT/US2004/042591.

PCT International Search Report dated May 26, 2008 for PCT Application No. PCT/US2007/025326.

PCT International Search Report dated May 29, 2008 for PCT Application No. PCT/US2007/025319.

PCT International Search Report dated Jun. 11, 2008 for PCT Application No. PCT/US2007/025329.

Peri, Francesca et al., "Preparation of Bicyclo[3.2.0]heptane-2-endo,7-endo-diols: 1,3-Diols with a Chiral Rigid Backbone," *J. Org. Chem.*, 69 (4):1353-1356 (2004).

Pines, Seemon et al., "Substituent Effects in the Reaction of N-Benzoyl-β-arylserinates with Thionyl Chloride," *J. Org. Chem.* 37:292-97(1972).

Pulido, Rosalino et al., "Enzymatic regioselective alkoxycarbonylation of hexoses and pentoses with carbonate oxime esters," *J. Chem. Soc. Perkin Trans. 1*, 5:589-592 (1993).

Rebstock, M.C. et al., "Chloramphenicol (Chloromycetin). IV. Chemical Studies," *J. Am. Chem. Soc.* 71:2458-62 (1949).

Rege, K. et al., "Chemoenzymatic synthesis and high-throughput screening of an aminoglycoside-polyamine library: identification of high-affinity displacers and DNA-binding ligands," *J Am Chem Soc.* 126(39):12306-15 (2004).

Schirmesiter, Helga et al., "Nucleosides. Part II the 2-(4-nitrophenyl) ethoxycarbonyl (npeoc) and 2-(2-,4-dinitrophenyl)ethoxycarbonyl (dnpeoc) groups for protection of hydroxy functions in ribonucleosides and 2-deoxyribonucleosides," *Helv. Chim. Acta* 76(1):385-401 (1993).

Shaw, W.V. et al., "Chloramphenicol Resistance by Enzymatic Acetylation: Comparative Aspects," *Antimicrobial Agents and Chemotherapy* 257-63(1968).

Shue, Youe-Kong et al., "Novel methodology for the synthesis of trans-alkene dipeptide isosteres," *J. Org. Chem.* 56(6):2107-2111 (1991).

Snyder et al., "Common bacteria whose susceptibility to antimicrobials is no longer predictable," *Leb. Med. J.* 48(4):208-214 (2000).

Supniewski et al., "Synthesis and Biological Properties of 1-Methylseleno-p-diphenyl-2-dichloroacetannino-1,3-propanediol" Bulletin de l'Academie Polonaise des Sciences, Serie des Sciences Biologiques 9, 231-234 (1961).

Supniewski et al., "Synthesis and Biological Properties of 1-Methylthio-p-diphenyl-2-dichloroacetamino-1,3-propanediol" Bulletin de l'Academie Polonaise des Sciences, Serie des Sciences Biologiques 9, 235-239 (1961).

Takamizawa, A. et al., "Studies of the Pyrimidine Derivatives. XXV.* The Reaction of Alkoxycarbonylthiocyanates and Related Compounds with the Sodium Salt of Thiamine," *Bull. Chem. Soc. Jpn.* 36(9):1214-1220 (1963).

Ti, T. et al., "Chloramphenical Concentrations in Sera of Patients with Typhoid Fever Being Treated with Oral or Intravenous Preparation", *Antimicrobial Agents and Chemotherapy*, 34(9):1809-1811 (1990).

Von Strandtmann, Maximilian et al.,"Synthesis of p-acyl analogs of chloramphenicol and their antimicrobial properties," *J Med Chem.* 10(5):888-90 (1967).

Wang, Haiyan et al., "Solid phase synthesis of neutral oligonucleotide analogues," *Tetrahedron Lett.* 32(50): 7385-7388 (1991).

Weber N. et al., "Steryl and stanyl esters of fatty acids by solvent-free esterification and transesterification in vacuo using lipases from *Rhizomucor miehei*, *Candida antarctica*, and *Carica papaya*," J Agric Food Chem. 49(11):5210-6 (2001).

Whalen, Lisa J. et al., "Resolution of a chiral alcohol through lipase-catalyzed transesterification of its mixed carbonate by poly(ethylene glycol) in organic media," Tetrahedron: asymmetry 11(6):1279-1288 (2000).

Wuts, Peter G. et al., "New Process for the Preparation of Methyl Carbonates," Org. Lett. 5(9):1483-1485 (2003).

Yu, Kuo-Long et al., "Retinoic Acid Receptor β, γ-Selective Ligands: Synthesis and Biological Activity of 6-Substituted 2-Naphthoic Acid Retinoids," J. Med. Chem. 39:2411-21(1996).

Zheng, Hu, "*Pharmaceutical Chemistry*", People's Medical Publishing House, Fourth Ed., p. 476; (Jul. 2002). (In Chinese language only).

Zheng, Hu, "*Pharmaceutical Chemistry*", People's Medical Publishing House, Fourth Ed., p. 476; (Jul. 2002). (English Translation of "FW").

* cited by examiner

WATER-SOLUBLE PRODRUGS OF FLORFENICOL AND ITS ANALOGS

CROSS-REFERENCE TO RELATED APPLICATIONS

This application is a non-provisional application that claims priority under 35 U.S.C. §119(e) of provisional application U.S. Ser. No. 60/874,864 filed Dec. 13, 2006, the contents of which are hereby incorporated by reference in its entirety.

FIELD OF THE INVENTION

The present invention relates to new prodrugs of florfenicol and analogs thereof. In one particular aspect, the present invention relates to charged nitrogen-containing esters of florfenicol and analogs thereof that demonstrate improved water solubility and hydrolytic stability. In a particular embodiment of this aspect, the present invention relates to certain charged nitrogen-containing esters of florfenicol.

BACKGROUND OF THE INVENTION

Florfenicol, 2,2-dichloro-N-((1R,2S)-3-fluoro-1-hydroxy-1-(4-(methylsulfonyl)phenyl)propan-2-yl)acetamide has the chemical structure

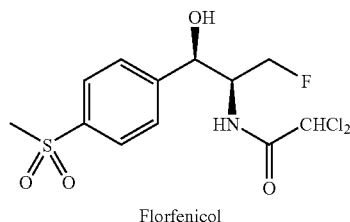

Florfenicol

Florfenicol is a broad spectrum antibiotic with activity against many gram-negative and gram-positive bacteria, including utility in the prevention and treatment of bacterial infections due to susceptible pathogens in birds, reptiles, fish, shellfish and mammals. One of florfenicol's primary uses is in the treatment of pneumonia and associated respiratory infections in cattle (often referred to generally as Bovine Respiratory Disease or BRD) caused by *Mannheimia haemolytica, Pasteurella multocida* and/or *Haemophilus somnus*, also known as *Histophilus somni*. It is also indicated in the treatment of: pododermatitis in cattle caused by *Fusobactrerium necrophorum* and *Bacteroides melaninogenicus*; swine respiratory disease caused by *Pasteurella multocida, Actinobacillus pleuropneumoniae, Streptococcus suis, Salmonella cholerasuis* and/or *Mycoplasma* spp.; colibacillosis in chickens caused by *Escherichia coli*; enteric septicemia in catfish caused by *Edwardsiella ictaluri*; and furunculosis in salmon caused by *Aeromnonas salmonicida*. Other genera of bacteria that have exhibited susceptibility to florfenicol include *Enterobacter, Klebsiella, Staphylococcus, Enterococcus, Bordetella, Proteus* and *Shigella*. In particular, chloramphenicol-resistant strains of organisms, such as *K. pneumoniae, E. cloacae, S. typhus* and *E. coli*, are susceptible to florfenicol.

Florfenicol is most often administered to subjects either orally or parenterally, the latter being primarily intramuscular or intravenous. Due to its very low water solubility (approximately one mg/mL), organic solvents must be added to achieve the desired product concentration in a commercial formulation. Given the need for economical, single-dose treatment in the veterinary setting, there remains a need for new formulations of florfenicol at high concentrations. In addition, there is also a need for a form of florfenicol that is capable of maintaining effective plasma antibiotic levels for prolonged periods of time, in order to achieve improved economies in administration, e.g., to more readily provide single dose treatment, particularly in a veterinary setting. In addition there is a need for similar forms of florfenicol analogs.

One of the important applications is a treatment of bacterial infections by dosing the drug in drinking water given to animals. Such means of administration provides effective treatment of bacterial infection since florfenicol is reasonably well absorbed from the intestine and achieves necessary antibacterial systemic levels. However, as mentioned above, the aqueous solubility of florfenicol is quite limited; consequently the solubilization of florfenicol in water is slow. Achieving the desired concentrations in drinking water requires preparation of pre-dissolved florfenicol in form of a concentrate in a water-miscible organic solvent. Additionally, a water-soluble prodrug of florfenicol or of an analog of florfenicol that was easily dissolved directly in the drinking water for animals would be quite desirable.

The two other common phenicol antibiotics, chloramphenicol and thiamphenicol, contain two hydroxyl groups: one of a primary and one of a secondary alcohol type. A substantial amount of work has been carried out in producing water-soluble prodrugs of these two antibiotics by esterification of the more easily accessible primary alcohol rather than the hindered secondary alcohol group. Glycinates of these compounds have been extensively investigated. Some examples of such esters are disclosed in U.S. Pat. Nos. 3,740,411 and 3,770,889 (both of Akiyama et al.), British patent 1,263,116 of Sumitomo Chemical Co., and 3,405,165 and 3,475,470 (both of Rebstock et al.).

A much smaller amount of work has been carried out on the production of water-soluble prodrugs of florfenicol, which lacks a primary alcohol group. For instance, esters of florfenicol were described in U.S. Pat. No. 4,311,857 of Nagabhushan. This patent describes primarily aliphatic esters of florfenicol, and also discloses esters produced from several amino acids, particularly the glycinate, ornithate and lysinate esters. Such amino acid esters are also disclosed in U.S. Pat. No. 6,790,867 of Kohan et al. Murthy et al., U.S. published patent application 2005/014828, describes a number of esters of florfenicol with aliphatic carboxylic acids. Hecker et al., U.S. published patent application 2005/0182031, describes certain phosphate esters of florfenicol. However, there still remains a need for alternative forms of florfenicol that have additional beneficial features. (It should be noted that the citation of any reference herein should not be construed that such reference is available as "prior art" to the instant application.)

BRIEF SUMMARY OF THE INVENTION

In brief, this invention comprises certain novel prodrugs of florfenicol and/or of florfenicol analogs, as described herein, including prodrugs of pharmaceutically acceptable salts of florfenicol or of its analogs. These prodrugs comprise nitrogen-containing esters of the secondary alcohol group of florfenicol and of its analogs, and in particular embodiments, are sufficiently water-soluble to serve the functions needed of a prodrug of florfenicol or of a prodrug of a florfenicol analog. In a more particular embodiment, a certain subclass of the compounds also possesses the hydrolytic stability needed to maintain the prodrug in solution in the subjects system until appropriate conditions exist when the prodrug can hydrolyze releasing florfenicol or the florfenicol analog in question.

Other aspects of the invention comprise pharmaceutical formulations of the above-mentioned prodrugs of florfenicol or of an analog of florfenicol, or of their pharmaceutically acceptable salts, also comprising one or more pharmaceutically acceptable excipients or carriers. Still other aspects comprise a method for treating a subject with florfenicol or a florfenicol analog comprising administering to said subject an effective amount of a prodrug of florfenicol or of a florfenicol analog, or of a pharmaceutically acceptable salt of these, or a pharmaceutical composition containing the same according to this invention.

The present invention further provides pharmaceutical compositions that comprise prophylactically-effective amounts of the novel prodrugs of florfenicol, prodrugs of analogs of florfenicol, or pharmaceutically acceptable salts of either of these. The present invention also provides mixtures of these compounds. In addition, in certain pharmaceutical compositions, florfenicol itself may be included in combination with one or more novel prodrugs of florfenicol, and/or prodrugs of analogs of florfenicol of the present invention. The present invention further provides pharmaceutical compositions that comprise the novel prodrugs that are useful for metaphylaxis. The pharmaceutical compositions of the present invention can be administered to animals or fish in prophylactically-effective amounts, and/or for metaphylaxis, as a need and/or the practice merits. Corresponding methods of administering prophylactically-effective amounts of the pharmaceutical compositions of the present invention and/or for metaphylaxis, as a need and/or the practice merits, are also provided by the present invention. The present invention also provides methods of treating or preventing a disease or disorder in an animal in need thereof.

DETAILED DESCRIPTION OF THE INVENTION

The present invention provides novel prodrugs of florfenicol and/or of florfenicol analogs, including prodrugs of pharmaceutically acceptable salts of florfenicol or of its analogs. These prodrugs possess one or more advantageous properties such as: water solubility, hydrolytic stability in aqueous systems and/or the ability to become released in the gastric tract of the animal due to enzymatic action. In particular embodiments, the prodrug is not converted to the parent drug prematurely either in the dosing solution and/or in the intestine (when intended to be used for the improvement of oral absorption). In a more particular embodiment, the administration of a prodrug of the present invention to a subject produces the desired rate of the conversion to the parent drug when the prodrug reaches its intended destination.

Thus, a prodrug molecule containing a moiety that results in improvement in solubility but is not sufficiently chemically stable when dissolved may not achieve the desired effect.

If the parent drug is acceptably well absorbed from the gastrointestinal system then the intended effect of the prodrug may be simply the improved solubility in order to facilitate the administration (e.g. in drinking water) In such case the release of the parent drug in the gastric system from the prodrug may occur by one or both of two independent mechanisms: enzymatic hydrolysis due to the action of an intestinal enzyme or chemical hydrolysis triggered by increase of pH encountered in the intestine relative to the pH of the original dosing solution. The chemical release of the parent drug may be due to the hydrolysis of the ester bond facilitated by elevated pH or by the action of some prodrug moieties capable of intramolecular cyclization. Specifically, the parent drug release may be due to the intramolecular displacement of the parent drug by the primary or secondary amine of the prodrug triggered by the pH change.

Accordingly, the invention provides novel prodrugs of florfenicol or a florfenicol analog having the Formula (I), and pharmaceutically acceptable salts thereof:

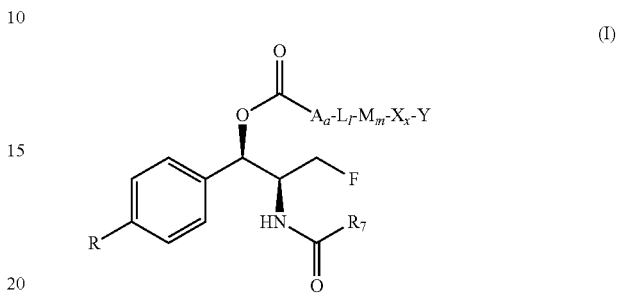

in which:
R is selected from the group consisting of

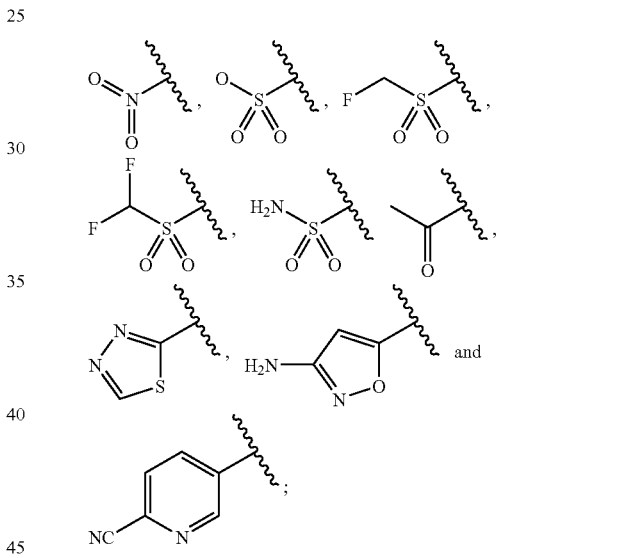

A is: oxygen and a is zero or 1;
L is:
(a) $CH_2$ and l is an integer from 1 to 6;
(b) $CHR_1$ where $R_1$ is an amino acid side chain and l is 1; or
(c) $CHR_1NHC(O)CH(NH_2)R_2$ where R and $R_2$ are amino acid side chains and l is 1;
M is:
(a) oxygen or sulfur and m is zero or one;
(b) $CH_2$ and m is zero or an integer from 1 to 4; or
(c) NH and m is 1;
X is:
(a) $CH_2$ and x is zero or an integer from 1 to 4; or
(b) C(O) and x is 1 and
Y is:
(a) $NH_2$;
(b) $NHR_x$ where $R_x$ is methyl, ethyl, n-propyl or isopropyl;
(c) $NR_yR_z$ where $R_y$ and $R_z$ are independently hydrogen, methyl, ethyl, n-propyl or isopropyl, or $R_y$ and $R_z$ taken together form a $C_2$-$C_5$ alkylene chain, or a $C_2$-$C_4$ alkylene chain further including a nitrogen or oxygen heteroatom in said chain;

(d) C(=NH)NH$_2$;
(e) N$^+$R$_5$R$_6$, where R$_4$, R$_5$ and R$_6$ are independently hydrogen, methyl or ethyl, or R$_4$ and R$_5$ taken together form a C$_2$-C$_5$ alkylene chain, or a C$_2$-C$_4$ alkylene chain further including a nitrogen or oxygen heteroatom in said chain.
(f) pyridinium;
(g) N-methyl or N-ethyl pyridinium;
(h) N'-3-methyl-N-1-imidazolium;
(i) a phenyl group substituted by a group having the formula NR$_4$R$_5$ or N$^+$R$_4$R$_5$R$_6$, where R$_4$, R$_5$ and R$_6$ are as defined above; or
(j) NH—CR$_3$(=NH) where R$_3$ is hydrogen, methyl or amino; and R$_7$ is selected from the group consisting of dichloromethyl, difluoromethyl, trifluoromethyl, cyanomethyl, azidomethyl, and aminomethyl;
provided that the group A$_a$L$_l$M$_m$X$_x$Y is other than an alpha-N-unfunctionalized glycine, ornithine or lysine residue.

In a particular embodiment of these compounds, the nitrogen atom of a prodrug moiety is a charged atom. Furthermore, in order to modulate the rate of hydrolysis of ester promoieties containing such a charged nitrogen atom or a sufficiently basic nitrogen atom assuring that the prodrug exists predominantly in charged form at the physiological pH, the nitrogen atom can be placed at a distance away from the carbonyl bond of the ester. The same effect can be achieved in carbonate derivatives containing a charged nitrogen atom by attaching the charged nitrogen atom further away from the hydrolyzable carbonate functionality. A charged nitrogen atom distance of at least two atoms, or at least three atoms, away from the carbonyl carbon atom of the ester or carbonate group to be hydrolyzed in the release of the parent drug is satisfactory for achieving the desired hydrolytic stability of the ester or carbonate.

Some preferred compounds of this invention, comprise the Formula (I):

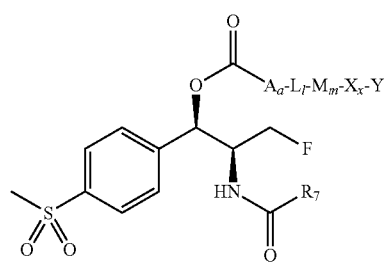

(II)

in which:
A is:
oxygen and a is zero or 1.
L is:
(a) CH$_2$ and l is an integer from 1 to 5; or
(b) CHR$_1$ where R$_1$ is an amino acid side chain and l is 1; or
(c) CHR$_1$NHC(O)CH(NH$_2$)R$_2$ where R$_2$ is an amino acid side chain and l is 1;
M is:
(a) oxygen and m is zero or one;
(b) CH$_2$ and m is zero or an integer from 1 to 4; or
(c) NH and m is 1;
X is:
(a) CH$_2$ and x is zero or an integer from 1 to 4; or
(b) C(O) and x is 1; and
Y is:
(a) NH$_2$;
(b) NHR$_x$ where R$_x$ is methyl, ethyl, n-propyl or isopropyl;

(c) NR$_y$R$_z$ where R$_y$ and R$_z$ are independently hydrogen, methyl, ethyl, n-propyl or isopropyl;
(d) C(=NH)NH$_2$;
(e) N$^+$R$_4$R$_5$R$_6$ where R$_4$, R$_5$ and R$_6$ are independently hydrogen, methyl or ethyl;
(f) N-pyridinium;
(g) N'-3-ethyl-N-1-imidazolium; or
(h) NH—CR$_3$(=NH) where R$_3$ is hydrogen, methyl or amino; and R$_7$ is selected from the group consisting of dichloromethyl, difluoromethyl, trifluoromethyl, cyanomethyl, azidomethyl, and aminomethyl; (with R$_7$ preferably being dichloromethyl);

provided that the sum of a+l+m+x is from 2 to 6, and preferably from 3 to 6;
provided that if a is 1, then M is (CH$_2$)$_m$; and
provided that the group A$_a$L$_l$M$_m$X$_x$Y is other than an alpha-N-unfunctionalized glycine, ornithine or lysine residue.

The present invention further provides pharmaceutically acceptable salts of these preferred compounds.

Particular compounds are those of Formula (I) or (II) in which Y includes a positively charged nitrogen atom. i.e., Y is a group N$^+$R$_4$R$_5$R$_6$ where R$_4$, R$_5$ and R$_6$ are independently hydrogen, methyl or ethyl such as NH$_3^+$, N$^+$H$_2$ (CH$_3$), N$^+$H (CH$_3$)$_2$, N$^+$(CH$_3$)$_3$, N$^+$H$_2$(C$_2$H$_5$), N$^+$H(C$_2$H$_5$)$_2$, N$^+$(C$_2$H$_5$)$_3$, 1-NH$^+$-3-methylimidazolium. Compounds in which a is zero are esters; those in which a is 1 are carbonates. Other particular compounds are those of Formula (I) or (I) in which the group A$_a$L$_l$M$_m$X$_x$Y is other than an alpha-N-unfunctionalized residue of an alpha-amino acid or of an aromatic alpha-amino acid (for example, the group A$_a$L$_l$M$_m$X$_x$Y is not an alpha-N-unfunctionalized phenylalanine residue), or the group A$_a$L$_l$M$_m$X$_x$Y is other than an alpha-N-unfunctionalized alpha-amino acid, or the group A$_a$L$_l$M$_m$X$_x$Y is other than an alpha-amino acid residue.

Compounds of Formulas (II) and (II) include compounds in which the group
A$_a$-L$_l$-M$_m$-X$_x$—Y$_y$ is, e.g. as shown immediately below:
1. Dipeptide esters R=H, aminoacid sidechain

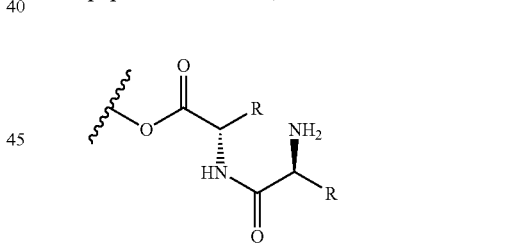

2. Omega amino esters (n=2-6) R=H, Me, Et

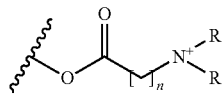

3. Omega amidino esters N-linked (n=2-6) R=H, Me

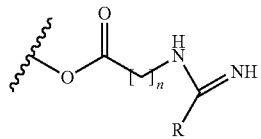

4. Omega amidino esters, C-linked (n=2-6)

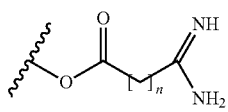

5. Omega guanidine esters (n=2-6)

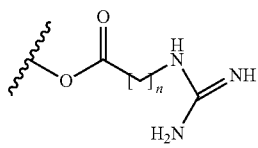

6. Omega amino acid esters-cyclic amines (n$_1$=1-6; n$_2$=2-4)

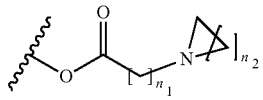

7. Omega quaternary ammonium esters (n=1-6) R=Me, Et

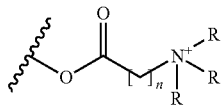

8. Omega quaternary ammonium esters-cyclic amines (n$_1$=2-6; n$_2$=2-4; R=Me, Et)

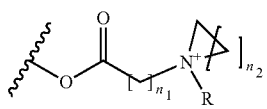

9. Omega quaternary ammonium esters-cyclic diamines (n=2-6; R=Me, Et)

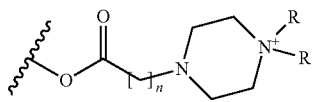

10. Omega pyridinium salts C-linked; (n=2-6; R=Me, Et)

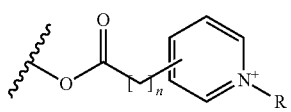

11. Omega imidazolium salts (n=2-6; R=Me, Et)

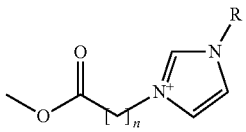

12. Aminomethyl benzoates (R=Me, Et)

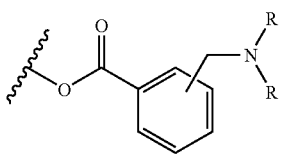

13. Quaternary salts of aminomethyl benzoates (R=Me, Et)

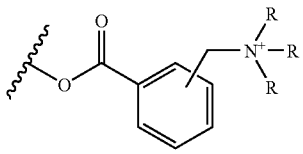

For types 2-11, also

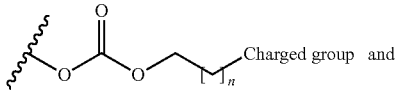

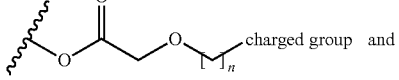

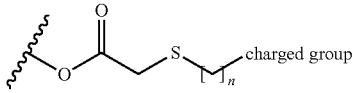

versions, where "charged group" represents a positively charged nitrogen-containing moiety of the type indicated.

Compounds of Formula (II) include, in general, and as exemplified below:
  A. Carbonates with a terminal amine functionality;
  B. Esters with an additional alpha-heteroatom (O,S) in the linker; for instance —C(O)CH$_2$OCH$_2$CH$_2$NH$_2$, C(O)CH$_2$SCH$_2$CH$_2$NH$_2$;
  C. Esters with an additional alpha-heteroatom (N)—which are amino acid derivatives but do not bear a protonable amine at the alpha position; these are dipeptides, e.g., —C(O)CH$_2$NHC(O)CH$_2$NH$_2$ and —C(O)CH(Me)NHC(O))CH(Me)NH$_2$;

D. Esters with quaternary nitrogen atoms removed at least two methylene groups away from the carbonyl group, for example C(O)CH$_2$CH$_2$CH$_2$CH$_2$—N-methylimidazolium and C(O)CH$_2$CH$_2$CH$_2$CH$_2$N$^+$Me$_3$.

Some preferred compounds are shown below:
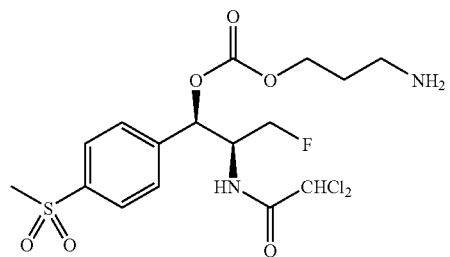
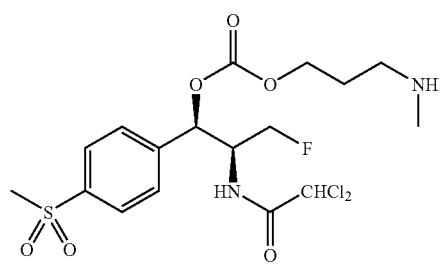
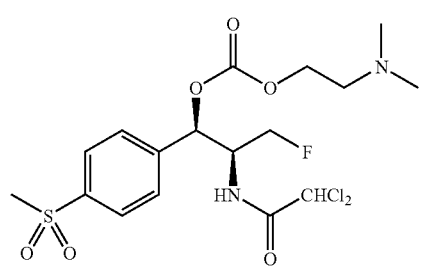
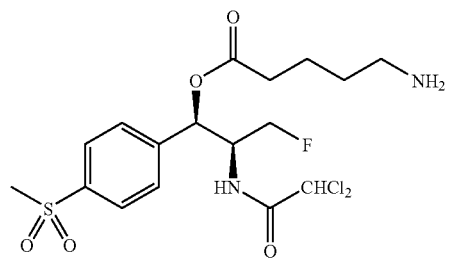
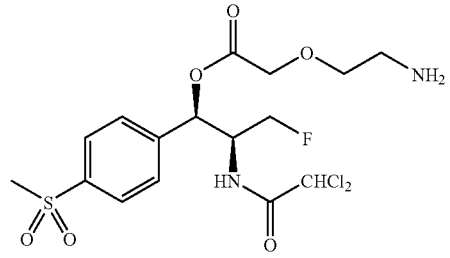
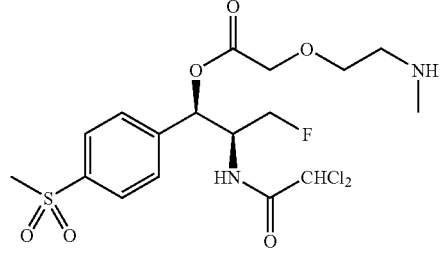
-continued
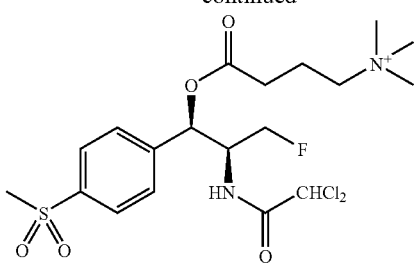
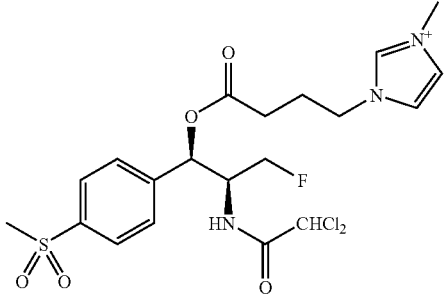
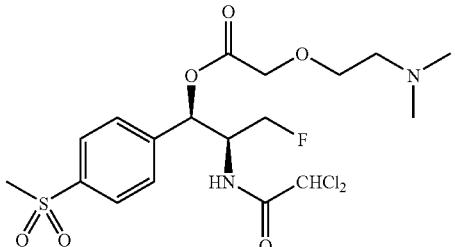
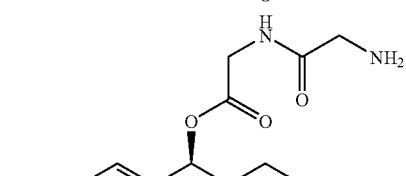
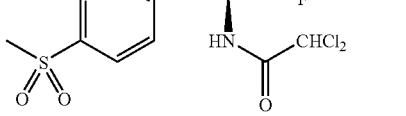
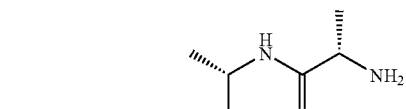
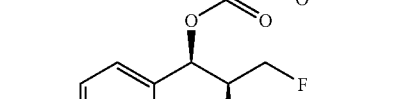
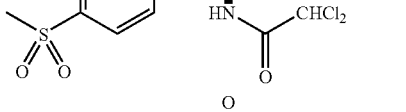
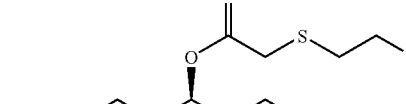
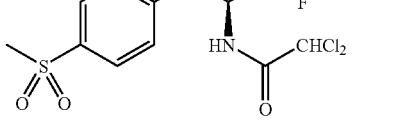

In another aspect, this invention relates to processes for preparing the novel compounds. In one process, compounds of the invention that are esters may be prepared by reacting florfenicol or a florfenicol analog with a carboxylic acid or a derivative thereof having a terminal group W which represents a protected primary or secondary amine that is later deprotected to a free amine, a tertiary amine, or a group that is later manipulated into a required charged nitrogen functionality. A commercially available activated derivative of the carboxylic acid may be used for the formation of the ester; it may be prepared in a separate reaction step or it may be prepared in situ in presence of the florfenicol or florfenicol analog

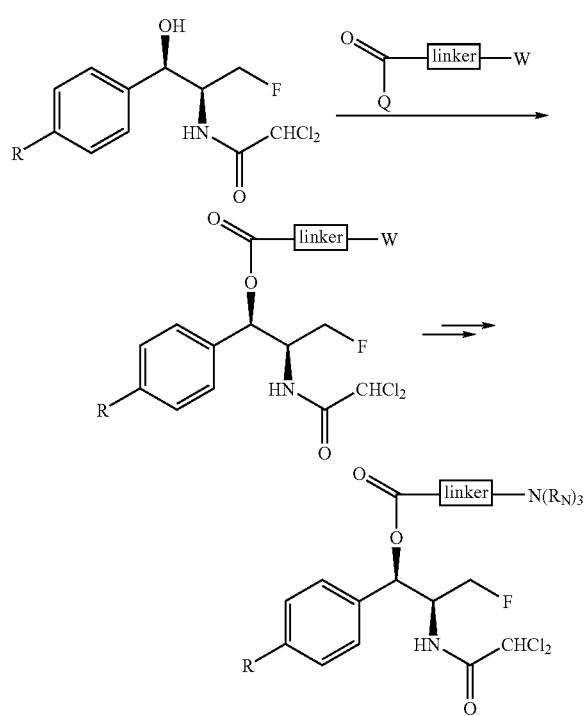

Compounds of the invention that are carbonates are prepared by reacting the florfenicol or florfenicol analog with a derivative of an alkoxycarbonic acid, for example a chloroformate having a terminal group W which represents a protected primary or secondary amine that is later deprotected to a free amine, a tertiary amine, or a group that is later manipulated into a required charged nitrogen functionality:

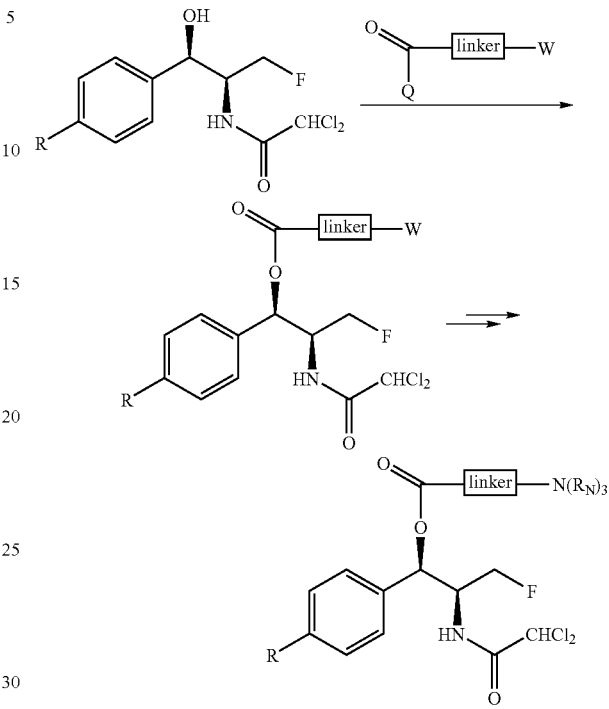

The necessary acids or chloroformates, if not commercially available, can readily be prepared by methods known to those in the art. Appropriate reaction conditions, solvents, etc., are exemplified below.

As shown in the above reaction schemes the secondary alcohol functionality of florfenicol or a florfenicol analog is reacted with the activated carboxylic acid or alkoxy carbonic acid reagents by nucleophilic displacement of group Q. Most common reagents of this type utilize Q=chlorine but many other leaving groups known in the art may be also employed.

As alternative to chloroformates (Q=chlorine) other reagents with different leaving groups Q may be used for preparation of carbonates of florfenicol alcohols. Representative references are cited for each leaving group, each incorporated by reference herein.

| Value of Q | References |
| --- | --- |
| —F | Olofson, R. A.; Cuomo, John; Tetrahedron Lett.; 21; 1980; 819-822; Nongkunsarn, Pakawan; Ramsden, Christopher A.; J. Chem. Soc. Perkin Trans. 1; 2; 1996; 121-122. |
| —CN | Adickes et al; J. Prakt. Chem.; 2; 133; 1932; 313. Cen, Chuo; Layton, Mark E.; Sheehan, Scott M.; Shair, Matthew D.; J. Am. Chem, Soc.; 122; 30; 2000; 7424-7425. |
| —SCN | Takamizawa, A. et al.; Bull. Chem. Soc. Jpn.; 36; 9; 1963; 1214-1220. |
| —NCS | Takamizawa, A. et al.; Bull. Chem. Soc. Jpn.; 36; 9; 1963: 1214-1220. |
| —O-aryl or —O-aryl | Patent; Chininfabr. Zimmer & Co.; DE 117095. Weber, Nikolaus; Wetkamp, Petra; Mukherjee, Kumar D.; J. Agric. Food Chem.; 49; 11; 2001; 5210-5216. Kenar, James A.; Knothe, Gerhard; Copes, Ashley L.; J. Am. Oil Chem. Soc.; 81; 3; 2004; 285-291. |
| —NH—OH | Mindl, Jaromir; Halama, Ales; Ceraosek, Zdenek; Collect. Czech. Chem. Commun.; 61; 7; 1996; 1053-1063. |

-continued

| Value of Q | References |
|---|---|
| imidazole | Kryczka, Boguslaw; Bull. Soc. Chim. Belg.; FR; 101; 2; 1992; 147-158.<br>Iimori, Takamasa; Shibazaki, Takafumi; Ikegami, Shiro; Tetrahedron Lett.; 37; 13; 1996; 2267-2270<br>Whalen, Lisa J.; Morrow, Cary J.; Tetrahedron: Asymmetry; 11; 6; 2000; 1279-1288.<br>Kozikowski, Alan P.; Sun, Haiying; Brognard, John; Dennis, Phillip A.; J. Am. Chem. Soc.; 125; 5; 2003; 1144-1145<br>Peri, Francesca; Binassi, Enrico; Manetto, Antonio; Marotta, Emanuela; Mazzanti, Andrea; Righi, Paolo; Scardovi, Noemi; Rosini, Goffredo; J. Org. Chem.; 69; 4; 2004; 1353-1356.<br>Chmielewski, Marcin K.; Marchan, Vicente; Cieslak, Jacek; Grajkowski, Andrzej; Livengood, Victor; Muench, Ursula; Wilk, Andrzej; Beaucage, Serge L.; J. Org. Chem.; 26; 2003; 10003-10012. |
| imidazolium | Schirmeister, Helga; Himmelsbach, Frank; Pfleiderer, Wolfgang; Helv. Chim. Acta; 76; 1; 1993; 385-401.<br>Greiner, Beate; Pfleiderer, Wolfgang; Helv. Chim. Acta; 81; 8; 1998; 1528-1544.<br>Banerjee, Anamitro; Lee, Kwangjoo; Falvey, Daniel E.; Tetrahedron; 55; 44; 1999; 12699-12710. |
| —O—N-Succinimide | Shue, Youe-Kong; Carrera, George M.; Tufano, Michael D.; Nadzan, Alex M.; J. Org. Chem.; 56; 6; 1991; 2107-2111.<br>; Dubowchik, Gene M.; Mosure, Kathle Knipe, Jay O.; Firestone, Raymond A.; Bioorg. Med. Chem. Lett.; 8; 23; 1998; 3347-3352. |
| —O—N-Benzotriazole | Harada, Takeo; Yamada, Haruo; Tsukamoto, Hirokazu; Takahashi, Takashi; J. Carbohydr. Chem.; 14; 1; 1995; 165-170.<br>Li, Hong-Yu; Qiu, Yao-Ling; Moyroud, Elisabeth; Kishi, Yoshito; Angew. Chem. Int. Ed.; 40; 8; 2001; 1471-1475; Angew. Chem.; 113; 2001; 1519-1523. |
| —N-Benzotriazole-N-oxide | Wuts, Peter G. M.; Ashford, Scott W.; Anderson, Andrew M.; Atkins, Joseph R.; Org. Lett.; 5; 9; 2003; 1483-1486. |
| —O—N=CR$_2$ | Pulido, Rosalino; Gotor, Vicente; J. Chem. Soc. Perkin Trans. 1; 5; 1993; 589-592.<br>Moris, Francisco; Gotor, Vicente; J. Org. Chem.; 57; 8; 1992; 2490-2492.<br>Moris, Francisco; Gotor, Vicente; Tetrahedron; 49; 44; 1993; 10089-10098.<br>Diaz, Monica; Gotor-Fernandez, Vicente; Ferrero, Miguel; Fernandez, Susana; Gotor, Vicente; J. Org. Chem.; 66; 12; 2001; 4227-4232.<br>Rege, Kaushal; Hu, Shanghui; Moore, James A.; Dordick, Jonathan S.; Cramer, Steven M.; J. Am. Chem. Soc.; 126; 39; 2004; 12306-12315. |
| Ortho- or para-nitrophenol | Brunelle, Daniel J.; Tetrahedron Lett.; 23; 17; 1982; 1739-1742.<br>Bruch, Karsten von dem; Kunz, Horst; Angew. Chem.; 102; 12; 1990; 1520-1522.<br>Wang, Haiyan; Weller, Dwight D.; Tetrahedron Lett.; 32; 50; 1991; 7385-7388.<br>Iimori, Takamasa; Shibazaki, Takafumi; Ikegami, Shiro; Tetrahedron Lett.; 37; 13; 1996; 2267-2270. |
| 2,4-dinitrophenol | Castro, Enrique A.; Angel, Mauricio; Pavez, Paulina; Santos, Jose G.; J. Chem. Soc. Perkin Trans. 2; 12; 2001; 2351-2354. |

The reaction may be facilitated by the addition of a catalyst like a trialkylamine, pyridine, a 4-alkylpyridine, a 4-diaminoalkyl pyridine or a combination thereof. Formation of the initial ester or carbonate intermediate can be conveniently performed in a variety of solvents. Suitable solvents include, for example, chlorinated solvents such as dichloromethane and 1,2-dichloroethane; ester solvents such as ethyl acetate, isopropyl acetate, isoamyl acetate ethylene glycol diacetate, propylene glycol diacetate glycerol triacetate; monoether solvents such as diethyl ether, diisopropyl ether, methyl tert-butyl ether; polyether solvents such as ethylene glycol ethers, dimethyl ethylene glycol ether, diethylene glycol ethers: diethylene glycol dimethyl ether, diethylene glycol diethyl ether; formaldehyde acetal ethers such as dimethoxymethane, diethoxymethane, dibutoxymethane; cyclic ethers such as tetrahydrofuran, 1,3-dioxolane, 1,4-dioxane; ketone solvents such as acetone, methyl ethyl ketone, methyl isobutyl ketone mixed ether/ester solvents as represented by monoethers of ethylene and diethylene glycol such as 2-methoxyethyl acetate, 2-ethoxyethyl acetate, 2-(methoxy-ethoxy)ethyl acetate, and 2-(ethoxy-ethoxy)ethyl acetate.

Definitions

As used herein:

"About" generally signifies that a value is within twenty percent of the indicated value, unless otherwise indicated "Amino acid" refers to the known natural amino acids, especially those selected from alanine, cysteine, phenylalanine, glycine, histidine, isoleucine, lysine, leucine, methionine, asparagine, proline, glutamine, arginine, serine, threonine, valine, tryptophan, and tyrosine. "Amino acid side chain" and "amino acid residue" refer to a group derived from an alpha-amino acid and represents the $R_{aa}$ group in the $NH_2$—$CH(R_{aa})CO_2H$ structure of the amino acid, for example —$CH(CH_3)_2$ for valine, —$CH_2CH_2CH_2CH_2NH_2$ for lysine and —CH$_2$OH for serine. For proline it represents —CH$_2$CH$_2$CH— which has its distal end attached to the alpha nitrogen atom. The term "alpha-N-unfunctionalized" refers to an amino acid residue with an unsubstituted —NH$_2$ group in the alpha position, as opposed to functionalized residues, in which for instance the alpha-amino group is a part of an amide bond of a peptide.

"Alkyl" refers to a straight or branched chain saturated hydrocarbon moiety having the number of carbon atoms designated (i.e. C$_1$-C$_{10}$ means one to ten carbons). Examples of alkyl groups include methyl, ethyl, n-propyl, isopropyl, n-butyl, t-butyl, isobutyl, sec-butyl, and the various pentyl, hexyl, heptyl, octyl, etc. groups. Alkyl groups also include those having one or more heteroatoms in the chain, e.g., methoxymethyl (CH$_3$OCH$_2$—), ethoxyethyl, methylthiomethyl (C$_3$SCH$_2$—), methylaminomethyl (CH$_3$NHCH$_2$—) and the like.

"Alkylene chain" refers to a divalent hydrocarbyl group derived from an alkyl group, i.e., a saturated straight or branched chain hydrocarbyl group linked at both of its ends to the remainder of the molecule in question. Typical alkylene groups include methylene, —CH$_2$—, ethylene, —CH$_2$CH$_2$— and n-propylene, —CH$_2$CH$_2$CH$_2$—. As with the alkyl groups, alkylene chains can include one or more hetero atoms. e.g., —CH$_2$CH$_2$—NH—CH$_2$CH— When an alkylene chain is combined with a nitrogen atom, as in groups having the formula NR$_y$R$_z$ the overall group is a heterocyclic group such as a piperidinyl, etc group. When the alkylene chain also includes a heteroatom, the resulting group NR$_y$R$_z$ would be, for instance, a cyclic moiety containing two nitrogen atoms such as a piperidinyl group.

"Prodrug" denotes a compound that is a drug precursor which, upon administration to a subject, undergoes chemical conversion by metabolic or chemical processes to yield the active drug, e.g., a carbonate of florfenicol or a florfenicol analog is a prodrug that releases the florfenicol compound in vivo.

"Pharmaceutical composition" refers to a composition or formulation comprising a compound according to this invention, including pharmaceutically acceptable salts thereof, (e.g., a florfenicol prodrug) with a pharmaceutically acceptable excipient and/or carrier. In a particular embodiment, the carrier is a solvent (e.g., water).

"Excipient" refers to an inert substance added to a pharmacological composition to further facilitate administration of an active ingredient. Examples, without limitation, of excipients include calcium carbonate, calcium phosphate, various sugars and types of starch, cellulose derivatives, gelatin, vegetable oils and polyethylene glycols.

"Administer" or "administration" refers to the delivery of the compound or solvate of the present invention or of a pharmaceutical composition containing a compound of this invention to an organism for the purpose of treating or preventing a microbial infection.

"Therapeutically-effective amount," as used herein, refers to that amount of a prodrug of the present invention that will hydrolyze sufficiently rapidly and in sufficient amounts to provide florfenicol or a florfenicol analog in a concentration at which it can relieve to some extent one or more of the symptoms of a bacterial infection in a subject. In particular embodiment, a therapeutically-effective amount refers to that amount of a florfenicol prodrug of the present invention that, when administered to a subject, delivers florfenicol or a florfenicol analog to a subject in a sufficient plasma concentration to: (1) reduce, and preferably eliminate, the population of bacterial cells in a subject's body; (2) inhibit (i.e., slow, or preferably stop) proliferation of the bacterial cells; (3) inhibit (i.e., slow, preferably stop) spread of the bacterial infection; and/or (4) relieve (preferably eliminate) one or more symptoms associated with the infection.

"Florfenicol analog" refers to analogs of florfenicol having a substituent other than methylsulfonyl on the phenyl ring, as indicated by the designation "R" in Formulas (I) and (II), and/or where R$_7$ is a group other than dichloromethyl.

"Prophylactically-effective amount" refers to the amount of a prodrug of florfenicol, or of a florfenicol analog of the present invention, that provides, upon hydrolysis, a sufficient plasma concentration of florfenicol or the florfenicol analog to: (1) maintain a reduced level of a population of bacterial cells achieved by a previously administered therapeutically-effective amount of the prodrug or some other appropriate drug; (2) maintain the level of inhibition of the proliferation of bacterial cells achieved by administration of a therapeutically-effective amount of a drug; (3) maintain the degree of inhibition of the spread of the infection achieved by a therapeutically-effective amount of a drug; and/or (4) maintain the level of relief of one or more symptoms, or if symptoms were eliminated, maintain the non-existence of symptoms associated with a bacterial infection achieved by administration of a therapeutically-effective amount of a prodrug (e.g., of florfenicol) of the present invention or some other appropriate drug. A prophylactically-effective amount also refers to that amount of a composition comprising a florfenicol prodrug, or a prodrug of a florfenicol analog, of the present invention, that will deliver florfenicol, or the florfenicol analog, in a sufficient plasma concentration to prohibit bacteria from accumulating in a susceptible organism in sufficient quantity to cause an infection.

Metaphylaxis is the timely mass medication of an entire group of animals to eliminate or minimize an expected outbreak of disease. e.g., in one or more animals at high risk of infection. In one particular embodiment, high risk calves are light weight, comingled with long haul cattle with unknown health histones.

As used herein the term "Minimum Inhibitory Concentration" is used interchangeably with "MIC". An "MIC$_{50}$" is the concentration of the compound (e.g., the prodrug of the present invention) at which the growth of 50% of the isolates is inhibited. Similarly, MIC$_{90}$ is the concentration of the compound at which the growth of 90% of the isolates is inhibited.

"Subject" refers to an animal species or fish capable of being infected by a pathogenic bacterium, and in a particular embodiment includes humans. Appropriate animal subjects also include those in the wild, livestock (e.g., raised for meat, milk, butter, eggs, fur, leather, feathers and/or wool), beasts of burden, research animals, companion animals, as well as those raised for/in zoos, wild habitats and/or circuses.

In a particular embodiment a "subject" of the invention is a "food producing" animal. For purposes of the present invention, the term "food-producing" animal shall be understood to include all animals bred for consumption or for consumables (e.g., dairy cows, egg-laying hens and the like) by humans and/or other animals. A non-limiting list of such animals include avian (chickens, turkeys, geese, duck, ostriches, etc.), bovines (e.g., cattle, dairy cows, buffalo), ovines (e.g., goats or sheep), porcines (e.g., hogs or pigs), equines (e.g., horses) etc., as well as aquatic animals including shellfish and fish such as trout or salmon, and other species raised or harvested for human consumption. For purposes of the present invention, the term "fish" shall be understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping.

Examples of potential fish recipients include the Salmonidae family, the Serranidae family, the Sparidae family, the Cichlidae family, the Centrarchidae family, the three-Line Grunt (*Parapristipoma trilineatum*), and the Blue-Eyed Plecostomus (*Plecostomus* spp).

In another embodiment, the subject is a companion animal. For purposes of the present invention, the term "companion" animal shall be understood to include housecats (feline), dogs (canine), rabbit species, horses (equine), rodents (e.g., guinea pigs, squirrels, rats, mice, gerbils, and hamsters), primates (e.g., monkeys) and avians, such as pigeons, doves, parrots, parakeets, macaws, canaries, and the like.

Other animals are also contemplated to benefit from the prodrugs of the present invention, including marsupials (such as kangaroos), reptiles (such as farmed turtles), game birds, swans, ratites and other economically important domestic animals.

Pharmaceutically acceptable salts of the compounds described above include hydrochloride, hydrobromide, methanesulfonate, sulfate, 2-hydroxyethylsulfate, citrate, and phosphate.

The following Table 1 depicts representative compounds of this invention.

with human patients; however, they readily may be modified for use with non-human patients by techniques well-known to those skilled in the veterinary art. Pharmaceutical compositions containing the novel compounds of this invention may also contain typical pharmaceutical excipients and additives such as liquid and/or solid carriers, surface-active agents, dispersants, taste-masking agents, and the like. Taste-masking agents include, for instance, those described for quinolones or their derivatives in U.S. Pat. No. 6,514,492 of Gao et al. (which is hereby incorporated by reference herein in its entirety), namely ion exchange resins (including both cationic and anionic resins) such as methacrylic acid-divinylbenzene copolymers (e.g., AMBERLITE® IRP-64), sodium polystyrene sulfonate resins (e.g., AMBERLITE® IRP-69), and polystyrene sulfonic acid-divinylbenzene resins (e.g., DOWEX® resins).

When the inventive compounds described herein are administered as a component of the feed of the animals, or dissolved or suspended in the drinking water, compositions are provided in which the active agent(s) are intimately dispersed in an inert carrier or diluent. An inert carrier is one that will not react with the inventive compound and one that may

TABLE 1

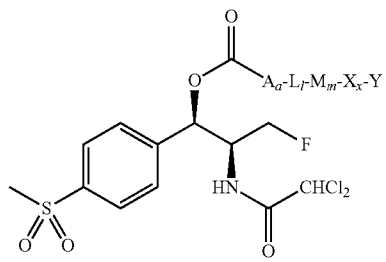

| Compound No. | $A_a$ | $L_l$ | $M_m$ | $X_x$ | Y |
|---|---|---|---|---|---|
| 1 | O | CH$_2$ | CH$_2$ | — | NH$_3^+$ [hydrochloride] |
| 2 | O | CH$_2$ | CH$_2$ | — | NH$_2^+$CH$_3$ [hydrochloride] |
| 3 | — | CH$_2$ | CH$_2$ | CH$_2$ | NH$_3^+$ [hydrochloride] |
| 4 | — | (CH$_2$)$_3$ | NH | CO | CH(NH$_3^+$)CH$_3$ [hydrochloride] |
| 5 | O | CH$_2$ | CH$_2$ | CH$_2$ | NH$_3^+$ [hydrochloride] |
| 6 | O | CH$_2$ | CH$_2$ | CH$_2$ | NH$_2^+$CH$_3$ [hydrochloride] |
| 7 | O | CH$_2$ | CH$_2$ | — | NH$_2^+$C$_2$H$_5$ [hydrochloride] |
| 8 | — | CH(NH$_3^+$) | (CH$_2$)$_2$ | CH$_2$ | NH$_3^+$ [di-hydrochloride] |
| 9 | — | CH$_2$ | NH | CO | CH$_2$NH$_3^-$ [hydrochloride] |
| 10 | — | (CH$_2$)$_4$ | — | — | NH$_3^+$ [hydrochloride] |
| 11 | — | CH(CH$_3$) | NH | CO | C(CH$_3$)NH$_3^+$ [hydrochloride] |
| 12 | — | (CH$_2$)$_4$ | — | — | NH$_2^+$CH$_3$ [hydrochloride] |
| 13 | O | CH$_2$ | CH$_2$ | CH$_2$ | NH$_2^+$C$_2$H$_5$ [hydrochloride] |
| 14 | — | CH$_2$ | O | (CH$_2$)$_2$ | NH$_3^+$ [hydrochloride] |
| 15 | — | CH$_2$ | CH$_2$ | CH$_2$ | N(CH$_3$)$_3^+$ [bromide] |
| 16 | — | CH$_2$ | CH$_2$ | CH$_2$ | N-3-methyl-N-1-imidazolium [bromide] |
| 17 | — | CH$_2$ | — | — | NH$_3^+$ [hydrochloride] |

Pharmaceutical Compositions

A compound of the present invention, or a physiologically acceptable solvate of the compound, may be administered as such to an animal in need thereof or may be administered in pharmaceutical compositions in which the foregoing materials are mixed with suitable excipient(s) or carriers. Techniques for formulation and administration of drugs may be found in *Remington's Pharmacological Sciences*, Mack Publishing Co., Easton, Pa., latest edition. The formulations and techniques discussed in Remington relate primarily to use be administered safely to animals. Preferably, a carrier for feed administration is one that is, or may be, an ingredient of the animal ration.

Suitable compositions include feed pre-mixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone, and the like. The inventive compound is intimately dispersed throughout the carrier by methods such as grinding, stirring, milling or tumbling. Compositions containing from about 0.05 to about 5.0% or, more broadly, from about 0.005 to about 2.0% by weight (w/w) of the inventive compounds are particularly suitable as feed pre-mixes. Feed supplements, which are fed directly to the animal, will contain from about 0.0002 to 0.3% by weight of the inventive compound.

Such supplements are added to the animal feed in an amount to give the finished feed the concentration of active compound desired for the treatment and control of susceptible microorganisms. Although the desired concentration of the inventive compound will vary depending upon the factors mentioned supra as well as upon the particular derivative employed, the compound is usually fed at concentrations of between about 0.0001 to 0.02% or from about 0.00001 to about 0.002% (both values as w/w) in the feed in order to achieve the desired antimicrobial result.

Pharmaceutical compositions of the present invention may be manufactured by processes well known in the art, e.g., using a variety of well-known mixing, dissolving, granulating, dragee-making, levigating, emulsifying, encapsulating, entrapping or lyophilizing processes. The compositions may be formulated in conjunction with one or more physiologically acceptable carriers comprising excipients and auxiliaries which facilitate processing of the active compounds into preparations which can be used pharmaceutically. Proper formulation is dependent upon the route of administration chosen.

For injection, including, without limitation, intravenous, intramuscular and subcutaneous injection, the compounds of the invention may be formulated in polar solvents including, without limitation, propylene glycol, alcohols, such as benzyl alcohol or ethanol, polyethylene glycol, and N-methyl-2-pyrrolidone, 2-pyrrolidone, other pyrrolidones, N,N-dimethylacetamide, N,N-dimethylformamide, dimethylsulfoxide, acetone, triacetin, glycerol, formal, triglycerides such as Miglyol® products optional water at concentrations up to 10%, as well as combinations of any of the foregoing excipients or other materials known to those of ordinary skill. For transmucosal administration, penetrants appropriate to the barrier to be permeated are used in the formulation. Such penetrants are generally known in the art.

In addition to the above-described formulations, concentrated compositions of compounds of the invention may be made, which may be diluted for use on site. Preparation of such concentrated compositions saves costs of shipping or storing large amounts of diluents, particularly water.

Administration

Suitable routes of administration may include, without limitation, oral, rectal, topical, transmucosal, intramuscular, subcutaneous, intramedullary, intrathecal, direct intraventricular, intravenous, intravitreal, intraperitoneal, intranasal, intramammary, aural or intraocular.

As discussed above, one method of administration of the compounds is by inclusion in the drinking water of the subject, since they are water-soluble.

Alternatively, one may administer the compound in a local rather than systemic manner, for example, by preparation as a salve or topically applied formulation that is applied directly to the infected area or by injection of the compound directly into infected tissue. In either case, a sustained release formulation may be used.

Thus, administration of the compounds of the invention, or their pharmaceutically acceptable solvates, in pure form or in an appropriate pharmaceutical composition, can be carried out via any of the accepted modes of administration or agents for serving similar utilities. The routes of administration can be any known to those of ordinary skill. The inventive compounds are given to those in need thereof in any art recognized form, i.e. solid, semi-solid, lyophilized powder, or liquid dosage forms, such as for example, tablets, suppositories, pills, soft elastic and hard gelatin capsules, powders, solutions, suspensions, or aerosols, or the like, in unit or multi-dosage forms suitable for simple administration of precise dosages. The compositions will include a conventional pharmaceutical carrier or excipient and a compound of the invention as the active agent, and, in addition, may include other medicinal agents, pharmaceutical agents, carriers, adjuvants, etc.

Dosage

A therapeutically effective amount refers to an amount of compound effective to prevent and/or minimize microbial infection, and/or treat alleviate and/or ameliorate symptoms due to a microbial infection. Determination of a therapeutically effective amount is well within the capability of those skilled in the art, especially in light of the disclosure herein.

For any compound used in the methods of the invention, the therapeutically effective amount can be estimated initially from known properties of the antibiotic agent that is released by the inventive prodrug compounds. Then, the dosage can be formulated for use in animal models so as to achieve a circulating concentration range that is at or greater than the minimum inhibitory concentration ("MIC") as previously known to the art. Such information can then be used to more accurately determine dosages useful in patients.

Therapeutic efficacy of the compounds described herein can be determined by standard pharmaceutical procedures in cell cultures or experimental animals. For example, the minimum inhibitor concentration ("MIC") is determined according to the guidelines laid down by the Clinical and Laboratory Standards Institute (CLSI)". Similarly, the toxicity of the compounds described herein can be depicted as $LD_{50}$ of the compound, which is a lethal dose for 50% of subjects in a group treated with a particular compound.

The data obtained can be used to formulate a range of dosages useful in patients. The dosage, of course, may vary depending upon the dosage form and route of administration. The exact formulation, route of administration and dosage can be selected by the individual clinician in view of the patient's condition. (See e.g., Fingl, et al., 1975, in "The Pharmacological Basis of Therapeutics", Ch. 1 p. 1). Broadly, the inventive compounds are administered to an animal in need of such treatment in a dose effective to reach and/or maintain concentrations of released antibiotic in plasma and body tissues at levels effective for the purpose, whether to treat and eliminate susceptible infectious microorganisms or to prevent new infection, for a sufficient time period to accomplish the desired goal. The skilled artisan will appreciate that the following estimated dose ranges are adjustable based on clinical response, as well as accounting for the relative amount of the antibiotic release from each respective prodrug compound. For example, for subcutaneous administration, the inventive compounds are generally administered at a dose ranging from about 1 mg to about 150 mg/kg of body weight. Frequency of administration can also range from a single dose per day to multiple doses per day. For oral administration, the dose will preferably be administered once per day.

Dosage amount and interval may be adjusted individually to provide plasma levels of the compound that are sufficient to maintain a concentration above or equal to the MIC or any other desired level. Such plasma levels are often referred to as minimum effective concentrations (MECs). The MEC will vary for each compound but can be estimated from in vitro data, e.g., the concentration necessary to achieve greater than 80% inhibition of a microbial population. The MEC may be ascertained using the assays described herein. Dosages necessary to achieve the MEC will depend on the individual characteristics of the compound and/or on the animal and/or route of administration. HPLC assays or bioassays can be used to determine plasma concentrations of the compound and/or its corresponding active product.

Dosage intervals can also be determined using MEC value. Compounds should be administered using a regimen that maintains plasma levels above the MEC for 10-90% of the time.

In cases of local administration or selective uptake, the effective local concentration of the drug may not be related to plasma concentration and other procedures known in the art may be employed to determine the correct dosage amount and interval.

The compositions may be administered once daily or divided into multiple doses. Often only one dose will be sufficient to treat the infection. In some circumstances one dose followed by a second dose 48 hours later will be required to treat the animal. The precise dose will depend on the stage and severity of the infection, the susceptibility of the infecting organism to the composition, and the individual characteristics of the animal species being treated, as will be appreciated by one of ordinary skill in the art.

The amount of a composition administered wilt, of course, be dependent on the patient being treated, pathogen or bacteria causing the infection, the severity of the infection, the manner of administration, i.e., oral, intravenous, topical, etc., and the judgment of the prescribing physician, veterinarian, etc.

The inventive compound will generally be administered at a dose ranging from about 1 mg to about 150 mg/kg body weight in cattle, when using the subcutaneous route. Preferably, the dose ranges from about 20 mg to about 70 mg/kg body weight. More preferably, the dose is about 60 mg/kg. However, when the inventive compound is administered via the intra-muscular (IM) route, the dose is preferably administered twice, with the administration of the second dose being about 24 to about 48 hours after the administration of the first dose.

In swine, the inventive compound will generally be administered in a dose ranging from about 10 mg to about 150 mg/kg body weight. Preferably the dose ranges from about 20 mg to 70 mg/kg body weight. In accordance with this invention, the prodrug is preferably administered to swine via their drinking water.

In poultry, the inventive compound will generally be administered in a dose ranging from about 10 mg to 150 mg/kg body weight. Orally, the prodrug will be administered in drinking water daily, for as long as is clinically indicated, e.g., for from about three to about seven days. In all the above cases, the prodrugs in drinking water can be administered either in a "bulk tank" or in a "proportioner". The final concentration will generally range from 50 mg/gallon to 700 mg/gallon. Preferably, the concentration ranges from about 100 mg/gallon to about 600 mg/gallon. More preferably, the final concentration is about 500 mg/gallon. Such administration of prodrugs in drinking water may continue for a period ranging from 1 to 10 days. More preferably, it will continue for 5 consecutive days, or until the symptoms of respiratory disease are under control.

Administration to Aquatic Animals

An embodiment of the invention includes methods of eliminating, reducing or preventing bacterial infections in fish or aquatic invertebrates. The methods include administering an effective amount of a compound of the invention to an aquatic animal in need thereof. In most aspects of this embodiment, administering is achieved by either feeding the animal an effective amount of the inventive compound or by immersing the animal or animal population in a solution which contains an effective amount of the active compound in solution. It is to be further understood that the inventive compound can be administered by application of the drug to a pool or other water-holding area containing the animal, and allowing the animal to absorb the compound through their gills or otherwise allowing the dosage of the inventive compound to be taken in. For individual treatment of specific animals, such as a particular fish, e.g., in a veterinary or aquarium setting, direct injection or injection of osmotic release devices comprising the inventive compound, alone or in combination with other agents, is an optional method of administering the inventive compound.

The dose of the inventive compounds that is effective for reducing eliminating, or preventing the bacterial infection in fish or other aquatic species can be routinely determined by a veterinarian using the parameters and methods discussed supra for other types of animals, although it may vary depending on the species of fish treated, the particular microorganisms involved, and the degree of infection. For aquaculture indications, the inventive compounds will generally be administered at a dosage of about 1 mg/kg to about 70 mg/kg and preferably from 10 mg/kg to 30 mg/kg. Suitable routes of administering include: intravenously, subcutaneously, intramuscularly and/or by spraying or dipping the aquatic species as needed, and/or by directly adding the compound into the water in a holding volume.

For oral administration, the inventive compounds may be administered at the doses specified above from about 10 to about 15 days.

While the active ingredient can be administered separately from food, it is contemplated that in a preferred aspect that the active will be incorporated into the fish feed. A medicated fish feed may be prepared by incorporating a suitable amount of compound of the present invention into a commercially available fish feed product to achieve the desired dosing levels. The amount of compound of the present invention incorporated into the fish feed will depend on the rate at which the fish are fed. For fish fed at the rate of about 0.2% to 4% of biomass/day, the medicated feed preferably contains from about 50 to 10,000 mg per kg of feed, and more preferably, from about 100 to 2,000 mg per kg of feed.

Although compounds of the present invention can be incorporated into a feed mixture prior to pelleting, the medicated feed is preferably formed by coating feed pellets with compound of the present invention.

Any fish species, including fresh water and salt water varieties, as well as invertebrate aquatic species, an enumerated hereinabove, can be treated with the compounds of the present invention to treat or prevent bacterial infections.

Combinations with Other Agents and Treatment Modalities

It is also contemplated to administer the inventive prodrug compounds in combination, simultaneously, or sequentially (e.g. in the same composition or in separate compositions) with other useful art-known medicinal agents. Such medicinal agents include, e.g., other microbiocides. e.g., antibiotics, antifungals, and antivirals, ecto- and endoparasiticides, and so forth, as well as nutritional supplements, feed additives and the like. For example it is contemplated to administer any art-known standard (non-prodrug) phenicol such as florfenicol, chloramphenicol or thiamphenicol themselves in combination with the inventive compounds. Processes for the manufacture of these antibiotic compounds, and intermediates useful in such processes, are described in U.S. Pat. Nos. 4,311,857; 4,582,918; 4,973,750; 4,876,352; 5,221,494; 4,743,700; 5,567,844; 5,105,009; 5,382,673; 5,352,832; and 5,663,361, hereby incorporated by reference. Other florfenicol analogs and/or prodrugs have been disclosed and such analogs also can be used in the compositions and methods of the present invention [see e.g., U.S. Pat. No. 7,041,670, and U.S. Pat. No. 7,153,842, both of which are hereby incorporated by reference in their entireties]. When the antibiotic compound is florfenicol, the concentration of florfenicol typically is from about 10% to about 50%, with the preferred level between about 20% and about 40%, even more preferred being at least about 30% (in these cases, given as w/w in the case of solid compositions and w/v in the case of liquid compositions).

Another useful antibiotic compound for use in a combination with the inventive compounds is tilmicosin. Tilmicosin is a macrolide antibiotic that is chemically defined as 20-dihydro-20-deoxy-20-(cis-3,5-dimethylpiperidin-1-yl)-desmycosin and which is reportedly disclosed in U.S. Pat. No. 4,820,695, hereby incorporated by reference. Also disclosed in U.S. Pat. No. 4,820,695 is an injectable aqueous formulation comprising 50% (by volume) propylene glycol, 4% (by volume) benzyl alcohol, and 50 to 500 mg/ml of active ingredient. Tilmicosin may be present as the base or as a phosphate. Tilmicosin has been found to be useful in treatment of respiratory infections, particularly *Pasteurella haemolytica* infections in cattle when administered by injection over a 4 day treatment period. Accordingly, tilmicosin may be used in treatment of, for example, neonatal calf pneumonia and bovine respiratory disease. When tilmicosin is present, it is present in an amount of about 1% to about 50%, w/v, preferably 10% to about 50%, and in a particular embodiment, 30%.

Another useful antibiotic for use in combination with the inventive compounds is tulathromycin. Tulathromycin may be prepared in accordance with the procedures set forth in U.S. Pat. No. 6,825,327, which is hereby incorporated by reference in its entirety. Tulathromycin may be present in injectable dosage forms at concentration levels ranging from about 5.0% to about 70% by weight. Tulathromycin is most desirably administered in dosages ranging from about 0.2 mg per kg body weight per day (mg/kg/day) to about 200 mg/kg/day in single or divided doses (i.e., from 1 to 4 doses per day), and more preferably 1.25, 2.5 or 5 mg/kg once or twice weekly, although variations will necessarily occur depending upon the species, weight and condition of the subject being treated. Tulathromycin may be present in injectable dosage forms at concentration levels ranging from about 5.0% to about 70% by weight (w/v).

Another useful antibiotic for use in combination with the inventive compounds is the fluoroquinlones family of antibiotics such as, for example, enrofloxacin, danofloxacin, difloxacin, orbifloxacin and marbofloxacin. In the case of enrofloxacin, it may be administered in a concentration of about 100 mg/ml. danofloxacin may be present in a concentration of about 180 mg/ml.

Other useful macrolide antibiotics for use in combination with the inventive compounds include compounds from the class of ketolides, or, more specifically, the azalides. Such compounds are described in, for example, U.S. Pat. Nos. 6,514,945, 6,472,371, 6,270, 768, 6,437,151 and 6,271,255, U.S. Pat. Nos. 6,239,112, 5,958,888, and U.S. Pat. Nos. 6,339,063 and 6,054,434, all of which are hereby incorporated by reference in their entireties.

Other useful antibiotics for use in combination with the inventive compounds include the tetracyclines, particularly chlortetracycline and oxytetracycline.

Other antibiotics may include beta-lactams such as one of the penicillins, e.g., penicillin G, penicillin K, ampicillin, amoxicillin, or a combination of amoxicillin with clavulanic acid or other beta-lactamase inhibitors. Additional particular beta-lactams include the cephalosporins such as, for example, ceftiofur, cefquinome, etc.

Additionally, the present invention optionally includes a composition for the treatment of a microbial and parasitic infection in an animal that comprises one or more of the above-listed antibiotics admixed and/or in combination with one or more of the inventive compounds, and an optional carrier and/or excipient.

For all of the methods and the inventive compounds described herein, it is also contemplated that the identified compounds are readily employed in combination with one or more art-known agents for killing or controlling various types of parasites, e.g., including all of the ecto- and endoparasites described herein. Thus, although the inventive compounds and methods are preferred over previously known agents and methods of using previously known agents, in certain optional embodiments they are contemplated to be employed in combination, simultaneously, or sequentially (e.g. in the same composition or in separate compositions), with other art-known agents or combinations of such art-known agents employed for killing or controlling various types of pests.

These additional agents for use in combination with the inventive compounds include, for ex ample, art-known anthelmintics, such as, for example, avermectins (e.g. ivermectin, moxidectin, milbemycin), benzimidazoles (e.g. albendazole, triclabendazole), salicylanilides (e.g. closantel, oxylozanide), substituted phenols, (e.g. nitroxynil), pyrimidines (e.g. pyrantel), imidazothiazoles (e.g. levamisole) and praziquantel.

Additional art-known agents for killing or controlling pests for use in combination with the inventive compounds include the organophosphate pesticides. This class of pesticides has very broad activity, e.g. as insecticides and, in certain instances, anthelmintic activity. Organophosphate pesticides include, e.g., dicrotophos, terbufos, dimethoate, diazinon, disulfoton, trichlorfon, azinphos-methyl, chlorpyrifos, malathion, oxydemeton-methyl, methamidophos, acephate, ethyl parathion, methyl parathion, mevinphos, phorate, carbofenthion, phosalone, to name but a few such compounds. It is also contemplated to include combinations of the inventive methods and compounds with carbamate type pesticides, including, e.g., carbaryl, carbofuran, aldicarb, molinate, methomyl, etc., as well as combinations with the organochlorine type pesticides. It is further contemplated to include combinations with biological pesticides, including e.g. repellents, the pyrethrins (as well as synthetic variations thereof, e.g., allethrin, resmethrin, permethrin, tralomethrin), and nicotine, that is often employed as an acaricide. Other contemplated combinations are with miscellaneous pesticides including: *Bacillus thuringiensis*, chlorobenzilate, formamidines, (e.g. amtitaz), copper compounds, e.g., copper hydroxide, cupric oxychloride sulfate, cyclotron, cypermethrin, dicofol, endosulfan, esenfenvalerate, fenvalerate, lambda-cyhalothrin, methoxychlor and sulfur.

In addition, for all of the methods and new compounds described herein, it is further contemplated that the identified compounds can be readily employed in combination with syngergists such as piperonyl butoxide (PBO) and triphenyl phosphate (TPP); and/or with Insect Growth Regulators (IGRs) and Juvenile Hormone Analogues (JHAs) such as diflubenzuron, cyromazine, methoprene, etc., thereby providing both initial and sustained control of parasites (at all stages of insect development, including eggs) on the animal subject, as well as within the environment of the animal subject.

Combinations with cyclodienes, ryania, KT-199 and/or older art-known anthelmintic agents, such as avermectins (e.g., ivermectin, moxidectin, milbemycin), benzimidazoles (e.g., albendazole, triclabendazole), salicylanilides (e.g., closantel, oxyclozanide), substituted phenols (e.g., nitroxynil), pyrimidines (e.g., pyrantel), imidazothiazoles (e.g., levamisole), praziquantel and some or organophosphates such as naphthalophos and pytaclofos, are also contemplated to be employed in such combinations.

In particular, additional antiparasitic compounds useful within the scope of the present invention are preferably comprised of the class of avermectin compounds. As stated above, the avermectin family of compounds is a series of very potent antiparasitic agents known to be useful against a broad spectrum of endoparasites and ectoparasites in mammals.

A preferred compound for use in combination with the inventive compounds within the scope of the present invention is ivermectin. Ivermectin is a semi-synthetic derivative of avermectin and is generally produced as a mixture of at least 80% 22,23-dihydroavermectin B1$_a$ and less than 20% 22,23-dihydroavermectin B1$_b$. Ivermectin is disclosed in U.S. Pat. No. 4,199,569, hereby incorporated by reference. Ivermectin has been used as an antiparasitic agent to treat various animal parasites and parasitic diseases since the mid-1980s.

Abamectin is an avermectin that is disclosed as avermectin B1a/B1b in U.S. Pat. No. 4,310,519, which is hereby incorporated by reference in its entirety. Abamectin contains at least 80% of avermectin B1$_a$ and not more than 20% of avermectin B1$_b$.

Another preferred avermectin is doramectin also known as 25-cyclohexyl-avermectin B$_1$. The structure and preparation of doramectin, is disclosed in U.S. Pat. No. 5,089,480, which is hereby incorporated by reference in its entirety.

Another preferred avermectin is moxidectin. Moxidectin, also known as LL-F28249 alpha is known from U.S. Pat. No. 4,916,154, which is hereby incorporated by reference in its entirety.

Another preferred avermectin is selamectin. Selamectin is 25-cyclohexyl-25-de(1-methylpropyl)-5-deoxy-22,23-dihydro-5-(hydroxyimino)-avermectin B$_1$ monosaccharide.

Milbemycin, or B41, is a substance which is isolated from the fermentation broth of a milbemycin producing strain of *Streptomyces*. The microorganism, the fermentation conditions and the isolation procedures are more fully described in U.S. Pat. Nos. 3,950,360 and 3,984,564.

Emamectin (4"-deoxy-4"-epi-methylaminoavermectin B$_1$), which can be prepared as described in U.S. Pat. No. 5,288,710 or 5,399,717, is a mixture of two homologues, 4"-deoxy-4"-epi-methylaminoavermectin B1a and 4"-deoxy-4"-epi-methylaminoavermectin B1b. Preferably, a salt of emamectin is used. Non-limiting examples of salts of emamectin which may be used in the present invention include the salts described in U.S. Pat. No. 5,288,710, e.g., salts derived from benzoic acid, substituted benzoic acid, benzenesulfonic acid, citric acid, phosphoric acid, tartaric acid, maleic acid, and the like. Most preferably, the Emamectin salt used in the present invention is emamectin benzoate.

Eprinomectin is chemically known as 4"-epi-Acetylamino-4"-deoxy-avermectin B$_1$. Eprinomectin was specifically developed to be used in all cattle classes and age groups. It was the first avermectin to show broad-spectrum activity against both endo- and ecto-parasites while also leaving minimal residues in meat and milk. It has the additional advantage of being highly potent when delivered topically.

The composition of the present invention optionally comprises combinations of one or more of the following antiparasite compounds (parasiticides):

The antiparasite imidazo[1,2-b]pyridazine compounds as described by U.S. Patent Application Publication No: 2005/0182059, incorporated by reference herein.

The antiparasite 1-(4-mono and di-halomethylsulphonylphenyl)-2-acylamino-3-fluoropropanol compounds, as described by U.S. Patent Application Publication No: 2005/0182139, incorporated by reference herein.

The antiparasite trifluoromethanesulfonanilide oxime ether derivative compounds, as described by U.S. Patent Application Publication No: 2006/0063841, incorporated by reference herein.

The antiparasite phenyl-3-(1H-pyrrol-2-yl)acrylonitrile compounds, as described by U.S. Patent Application Publication No. 2006/128779, incorporated by reference herein.

The antiparasite N-[(phenyloxyphenyl)-1,1,1-trifluoromethanesulfonamide and N-(phenylsulfanyl phenyl]-1,1,1-trifluoromethanesulfonamide derivatives as described by U.S. Patent Application Publication No. 2006/0281695, incorporated by reference herein.

The antiparasite N-phenyl-1,1,1-trifluoromethanesulfonamide hydrazone compounds as described by U.S. Patent Application Publication No. 2007/0238700, incorporated by reference, herein.

The compositions of the present invention may also be employed in combination with a flukicide. Suitable flukicides include, for example, triclabendazole fenbendazole, albendazole, clorsulon and oxibendazole. It will be appreciated that the above combinations may further include combinations of antibiotic, antiparasitic and anti-fluke active compounds.

In addition to the above combinations, it is also contemplated to provide combinations of the inventive methods and compounds, as described herein, with other animal health remedies such as trace elements, anti-inflammatories, anti-infectives, hormones, dermatological preparations, including antiseptics and disinfectants, and immunobiologicals such as vaccines and antisera for the prevention of disease.

For example, such antinfectives include one or more antibiotics that are optionally co-administered during treatment using the inventive compounds or methods, e.g., in a combined composition and/or in separate dosage forms. Art-known antibiotics suitable for this purpose include, for example, those listed hereinabove.

Further, it is also contemplated that the inventive methods and compounds be advantageously employed in combination, simultaneously or sequentially, with art-known animal health remedies e.g., trace elements, vitamins, anti-inflammatories, anti-infectives and the like, in the same or different compositions.

Suitable anti-inflammatory agents include, e.g., both steroidal and non-steroidal anti-inflammatory agents. Non-steroidal anti-inflammatory agents, including their racemic mixtures or individual enantiomers where applicable, can include ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate.

In a particular embodiment, a compound of the present invention is employed in combination with flunixin, [see, e.g., U.S. Pat. No. 6,790,867 B2, which is hereby incorporated by reference in its entirety.] In a related embodiment, the present invention provides a pharmaceutical composition comprising a compound of the present invention and flunixin.

Steroidal anti-inflammatory agents include, for example, glucocorticoid agents such as dexamethasone, cortisone, hydrocortisone, prednisone, beclomethasone, betamethasone, flunisolide, methyl prednisone, para methasone, prednisolone, triamcinolome, alclometasone, amcinonide, clobetasol, fludrocortisone, difluorosone diacetate, fluocinolone acetonide, fluoromethalone, flurandrenolide, halcinonide, medrysone, mometasone, and pharmaceutically acceptable salts and mixtures thereof.

Packaging

The compositions may, if desired, be presented in a pack, sachet, or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. In an optional embodiment, the packaging comprises glass or plastic vials or other containers comprising multiple doses.

The following represent examples of preparation of compounds of this invention. However, they are meant to be only illustrative of the invention and not limiting of it Synthesis of Water Soluble Prodrugs In the following schemes the "FFC-OH" and "FFC-O" symbols are used for florfenicol and for the oxygen-linked florfenicol moiety respectively:

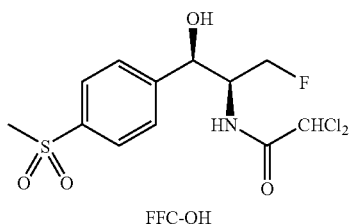

FFC-OH

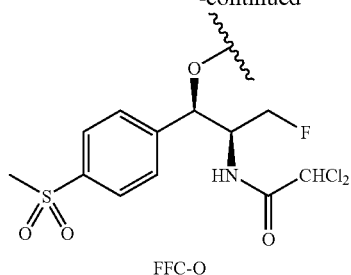

FFC-O

Florfenicol carbonates and florfenicol esters bearing a nitrogen based positively charged nitrogen functionality can be conveniently prepared by reaction of florfenicol with appropriately activated carboxylic acids or alkoxy carbonic acid reagents. These reagents can be prepared by generally known methods described in the literature (e.g. "March's Advanced Organic Chemistry: Reactions, Mechanisms, and Structure", 5th Edition Michael B. Smith, Jerry March, Jan. 15, 2001; Wiley-Interscience).

One strategy for preparation of the florfenicol carbonates and florfenicol esters bearing a nitrogen based positively charged nitrogen functionality employs the use of an appropriately protected amino functionality as shown in the Scheme 1 below (a large selection of protecting groups PG for amino group protection and methods for using them is described in "Protective Groups in Organic Synthesis", Theodora W. Greene, Peter G. M. Wuts; May 15, 1999 Wiley-Interscience).

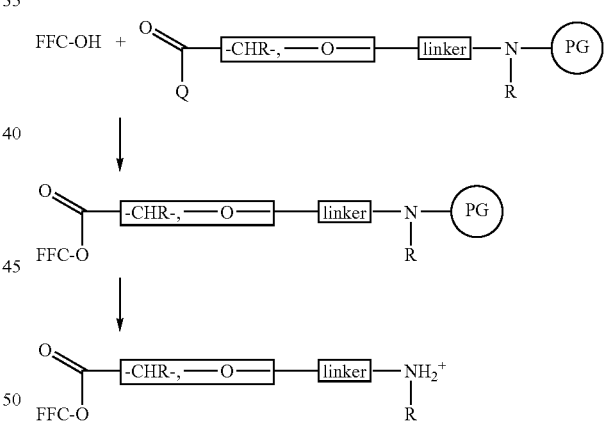

Scheme 1

Florfenicol is reacted with the activated carboxylic acid reagent (e.g., acyl chloride, acyl imidazolide, carboxylic acid hydroxysuccinimide ester, carboxylic acid perfluorophenol ester, carboxylic acid carbondiimide adduct and like) or activated alkoxy carbonic acid reagent (chloroformate or an alternative carbonating reagent having leaving group other than chloride-vide supra) with the nucleophilic displacement of group Q. Most common reagents of this type utilize Q=chlorine. The reaction may be facilitated by the addition of a catalyst like a trialkylamine, pyridine, a 4-alkylpyridine, a 4-diaminoalkyl pyridine or a combination thereof. Alternatively the carboxylic acid can be activated in situ by addition of the appropriate activating reagent to the reaction mixture containing florfenicol and the carboxylic acid. Formation of the initial ester or carbonate intermediate can be conveniently performed in variety of solvents. Suitable solvents include, for example, chlorinated solvents such as dichloromethane and 1,2-dichloroethane; ester solvents such as ethyl acetate, isopropyl acetate, isoamyl acetate, ethylene glycol diacetate, propylene glycol diacetate, glycerol triacetate; monoether solvents such as diethyl ether, diisopropyl ether, methyl tert-butyl ether; polyether solvents such as ethylene glycol ethers, dimethyl ethylene glycol ether, diethylene glycol ethers: diethyleneglycol dimethyl ether, diethylene glycol diethyl ether; formaldehyde acetal ethers such as dimethoxymethane, diethoxymethane, dibutoxymethane; cyclic ethers such as tetrahydrofuran, 1,3-dioxolane, 1,4-dioxane; ketone solvents such as acetone, methyl ethyl ketone, methyl isobutyl ketone; mixed ether/ester solvents as represented by monoethers of ethylene and diethylene glycol such as 2-methoxyethyl acetate, 2-ethoxyethyl acetate, 2-(methoxy-ethoxy)ethyl acetate, 2-(ethoxy-ethoxy)ethyl acetate. The examples provided below exemplify the use of tetrahydrofuran as the solvent.

Typically the reaction is conducted by adding 1.5-2.0 equivalents of corresponding chloroformate or other reactive alkoxycarbonic acid derivative in tetrahydrofuran solution to the tetrahydrofuran solution containing a phenicol, 1.0 equivalent of triethylamine and 0.5 equivalent of 4-N,N-dimethylaminopyridine at 0° C. and allowing the reaction to proceed to completion.

After formation of terminal amine protected ester or carbonate of florfenicol the deprotection of the amine functionality is performed by a standard deprotection method depending on the character of the protecting group. For acid-sensitive protecting groups the deprotection can lead directly to the desired salt form (e.g., hydrochloride) when the appropriate acid is used for deprotection. When the deprotection method produces the free amine (e.g., hydrogenolytic removal of benzyloxycarbonyl group) the desired salt form can be prepared by adding the acid to the reaction mixture or by performing conversion of the amine to the appropriate salt in a separate step.

A typical example of preparation of the water soluble florfenicol amine hydrochloride prodrug according to the invention is represented by preparation of the compound of Example 1

An alternative strategy for preparation of florfenicol carbonates and florfenicol ester prodrugs bearing a terminal nitrogen-based positively charged functionality may involve a nitrogen-containing "masked amine" functionality which is in a later stage converted into desired amine. Examples of typical nitrogen-containing functionalities for this purpose (and respective methods from conversions into amine) are: nitro (reduction), azido (reduction), nitrile (reduction to $CH_2NH_2$) and primary amide (Curtius rearrangement).

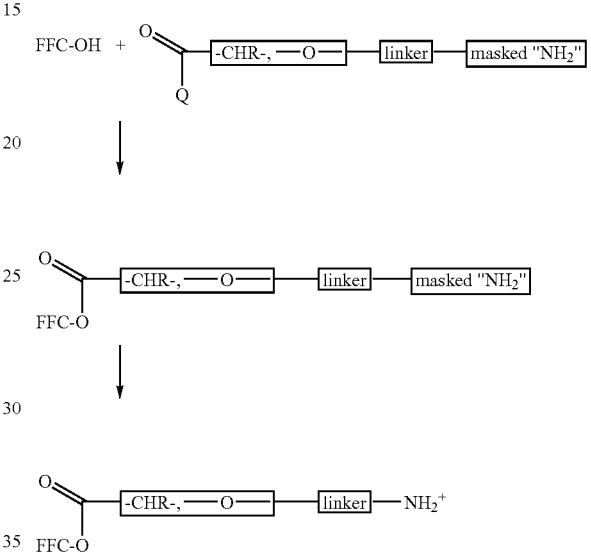

Scheme 2A below shows the method of preparation of the compound of Example 3 employing a masked nitrogen functionality which is convenient for this purpose:

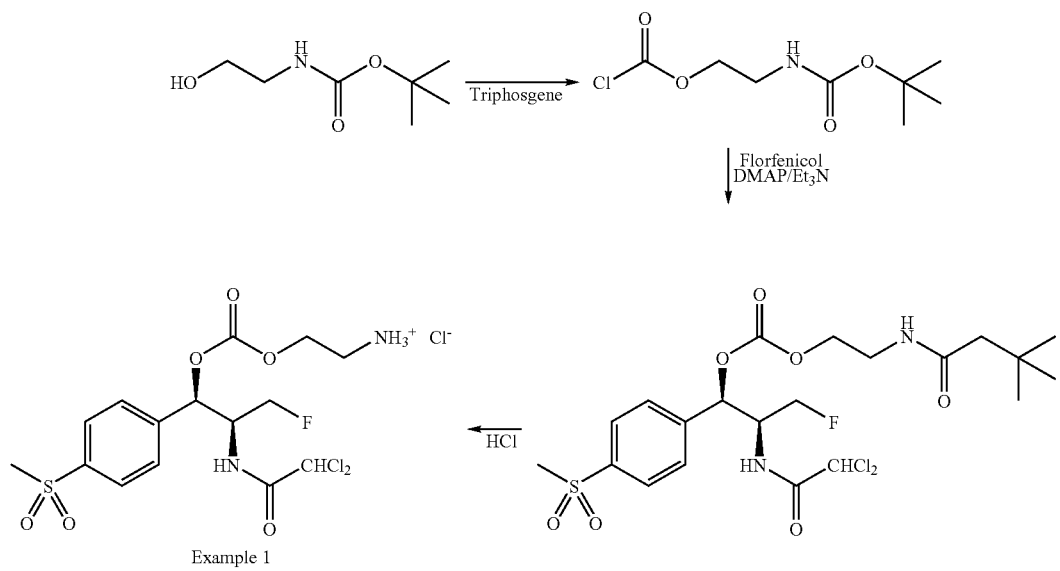

Example 1

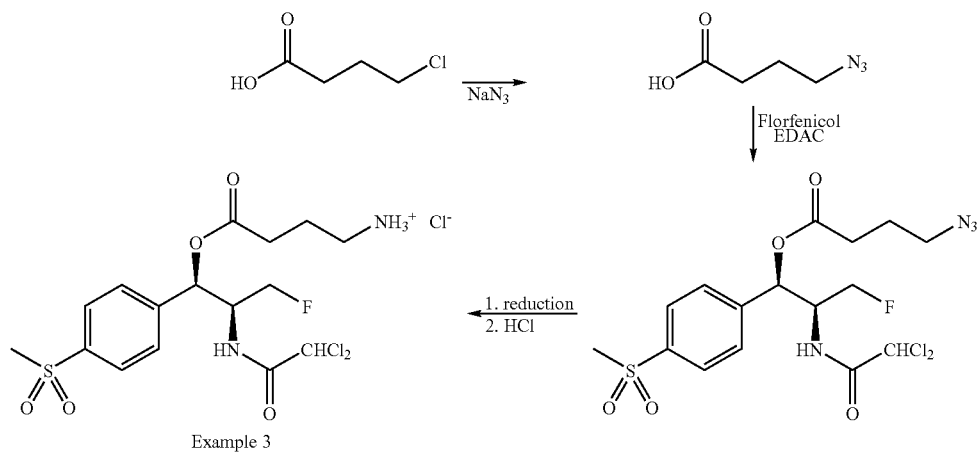

Another convenient strategy for preparation of the prodrugs of the present invention involves displacement of the leaving group LG on the carbonate or ester moiety attached to florfenicol. This approach can be particularly convenient for prodrug moieties bearing a quaternary ammonium nitrogen but it can be also used for the introduction of other amino functionalities.

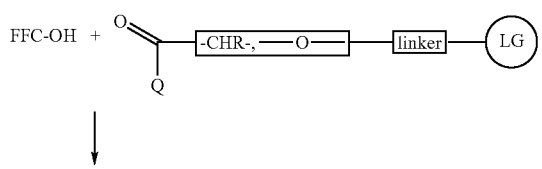

Scheme 3A below shows the application of such strategy to the preparation of prodrugs of Examples 15 and 16 in which the desired corresponding quaternary ammonium bromides can be obtained directly in the alkylation step.

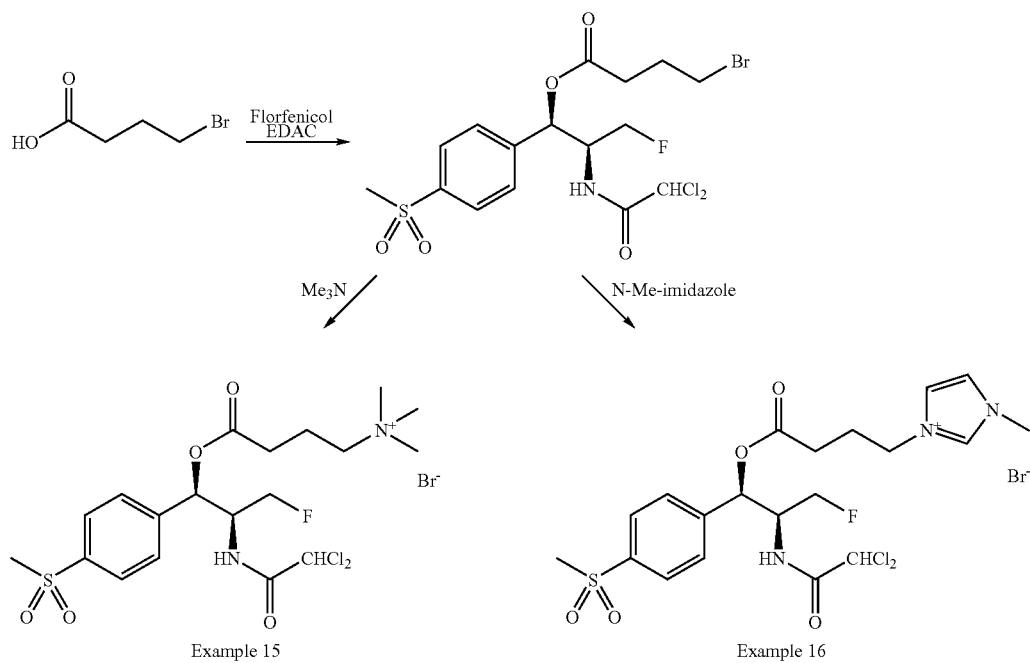

A convenient method for preparation of the amino acid ester prodrug of florfenicol may utilize combination of methods from Schemes 2A and 3A as shown below for the preparation of the compound of Example 17.

Scheme 4

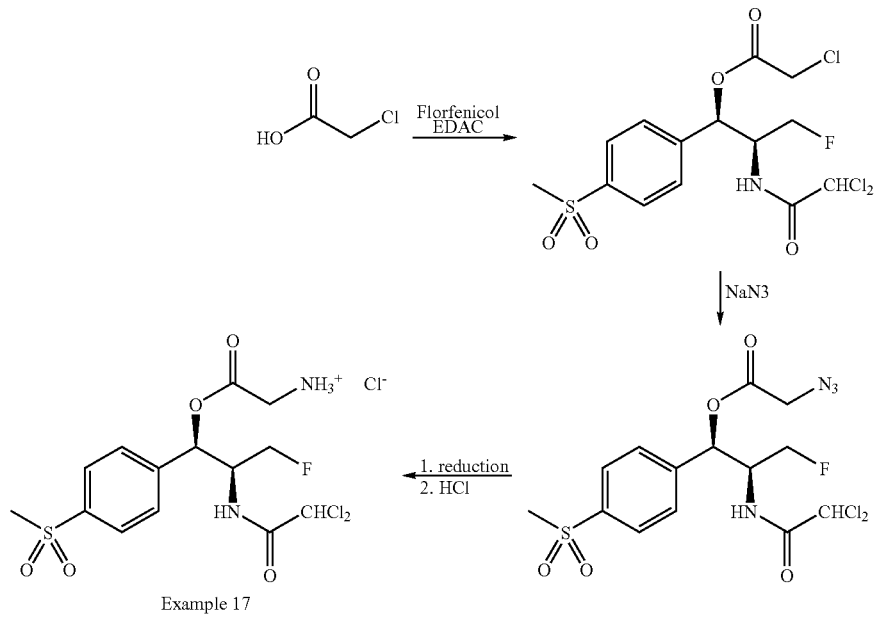

Example 17

For the preparation of florfenicol ester prodrugs which contain a basic or charged quaternary nitrogen which is part of an alpha-amino acid that is not directly attached to florfenicol at least two general strategies can be employed. In one strategy the distal amino acid is incorporated into the prodrug moiety before attaching it to florfenicol while in the other one the attachment of the distal amino acid can be performed after attaching the first fragment of the prodrug moiety to florfenicol.

The two strategies which can be conveniently used for preparation of such prodrugs are exemplified in Scheme 5 describing preparation of the compound of Example 4.

Scheme 5

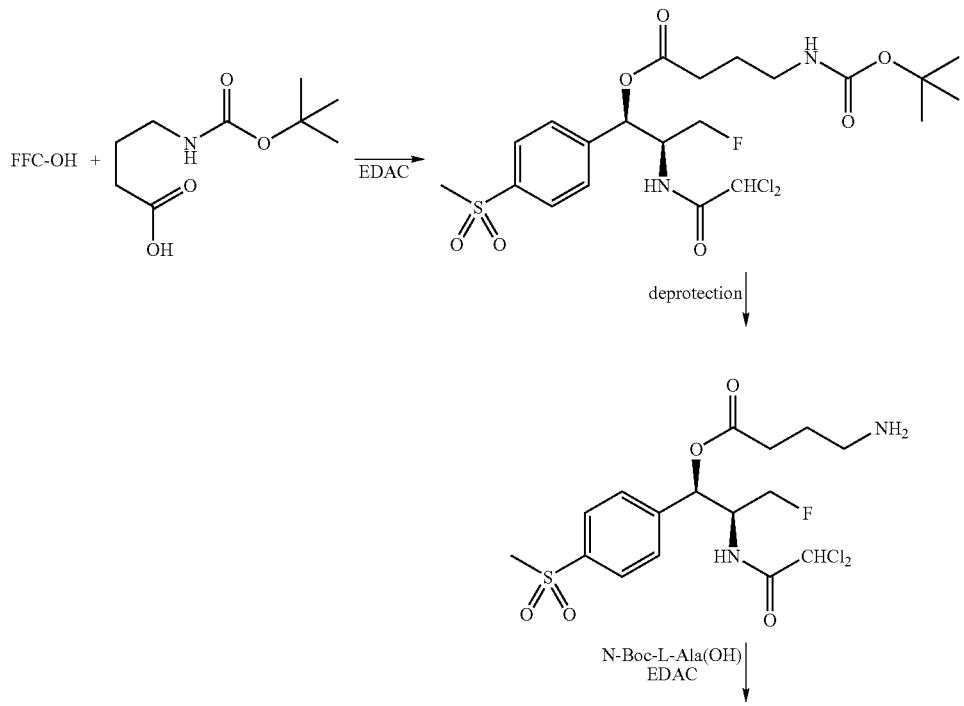

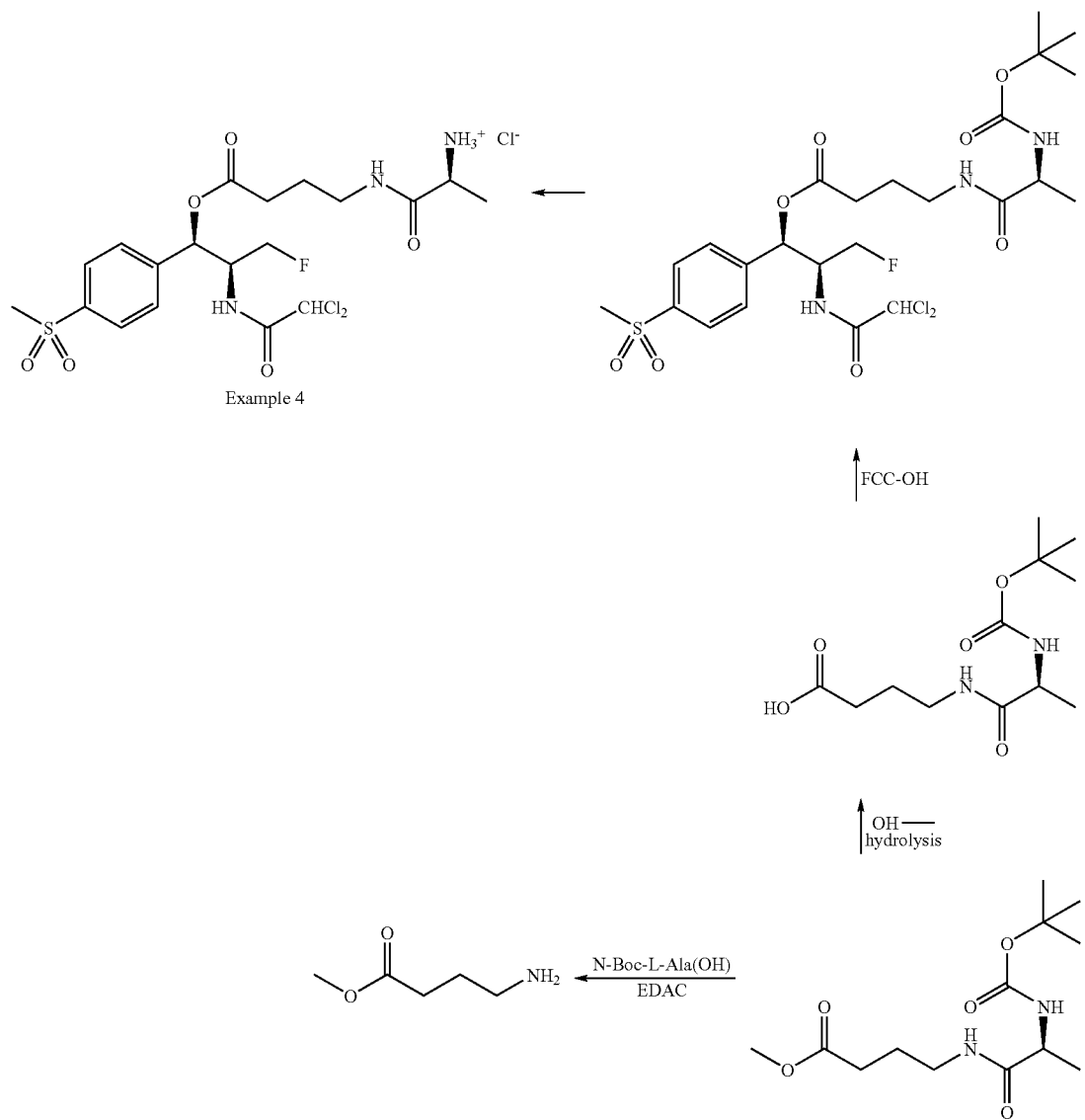
Stability of Prodrugs and Florfenicol Release
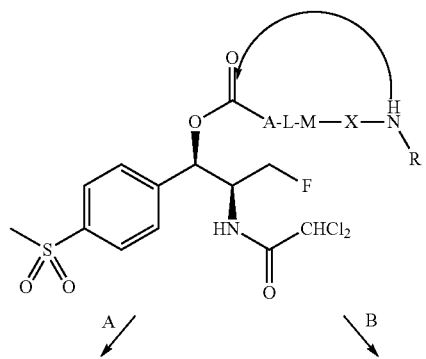

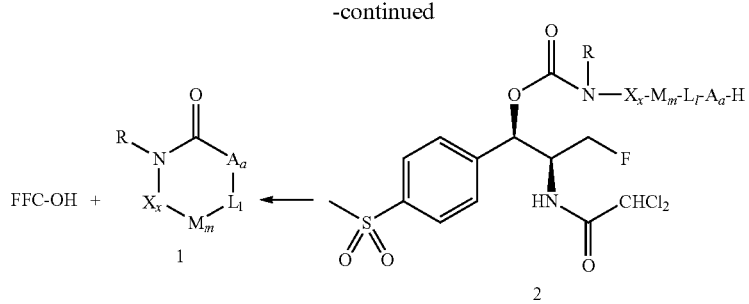

A non-enzymatic release of florfenicol can take place when there is a possibility of intramolecular displacement of florfenicol by the terminal amine functionality (Scheme 7, route A). The rates of such processes depend greatly on the substrate and the pH of the solution. For this displacement to occur the terminal amine needs to be primary or secondary and the pH needs to be sufficiently high to allow for the unprotonated amine to exist in unprotonated form in meaningful concentration. Additionally the sum of x+m+l+a needs to be 3 or 4 to allow easy formation of the 5 or 6-membered ring upon cyclization. Substitution of the terminal amine also can affect the rate of such cyclization mediated release of florfenicol dramatically. Acylation of the amine entirely prevents such cyclization while alkyl substitution can slow the cyclization considerably relative to the unsubstituted primary amine. According to the above criteria compounds of Examples 1-3 and 5-14 of this invention are capable of undergoing cyclization while compounds of Examples 4 and 15-17 of this invention cannot undergo such process. The ability to undergo cyclization and release florfenicol can largely determine the stability of prodrugs when the pH of the aqueous solution is adjusted from original pH of 4.5 observed for aqueous solutions of crude hydrochlorides of most prodrugs to close to the physiological pH of 7.4. Rates of such cyclizations in many cases are not fast enough to affect the stability of prodrug solutions in a meaningful way (see table 2) but in some cases the cyclizations can be quite rapid. Half-lives in the range from a few minutes to 3 hrs observed in pH 7.4 aqueous solutions for Examples 1-2, 7-9, 11 and 14 can largely be explained by the cyclization mediated florfenicol release.

Florfenicol or florfenicol analog release induced by a change of pH when the prodrug solution that has been given orally reaches the intestine is entirely acceptable from the standpoint of the oral bioavailability of florfenicol since it is well known that florfenicol itself is well absorbed orally. Depending on the rate of release of florfenicol after intestinal pH adjustment of the ingested prodrug solution, the release and absorption of free florfenicol may be responsible for varying degrees of bioavailability of florfenicol from different soluble prodrugs. For more stable prodrugs a major component of the oral bioavailability of florfenicol may be due to the oral absorption of intact prodrug followed by fast systemic release by an enzymatically mediated process.

A competing process induced by the change of the pH of the prodrug solution, which is only possible for carbonate prodrugs (A=oxygen), also occurs by the initial nucleophilic attack of the terminal primary or secondary amine on the carbonyl functionality linking the prodrug moiety to florfenicol (tertiary amines and quaternary ammonium groups can not participate in such transformations). In the case of carbonates a process of the rearranged acyclic carbamate formation (Scheme 7, route B; no release of florfenicol) can compete with the formation of cyclic carbamate (Scheme 7, route A; florfenicol release). In the in vitro evaluation of the prodrugs the formation of considerable amounts of the rearranged isomer of the prodrug was observed for Examples 1, 2 and 7 (see table 2). The carbonate prodrug of Example 6 did not show any formation of the rearranged isomer while for the carbonate prodrug of Example 5 the rearrangement was slow enough to produce only a small amount of rearrangement product in a pH 7.4 adjusted solution, but no rearrangement was observed in bovine serum.

General Procedure I
Preparation of Florfenicol Carbonates

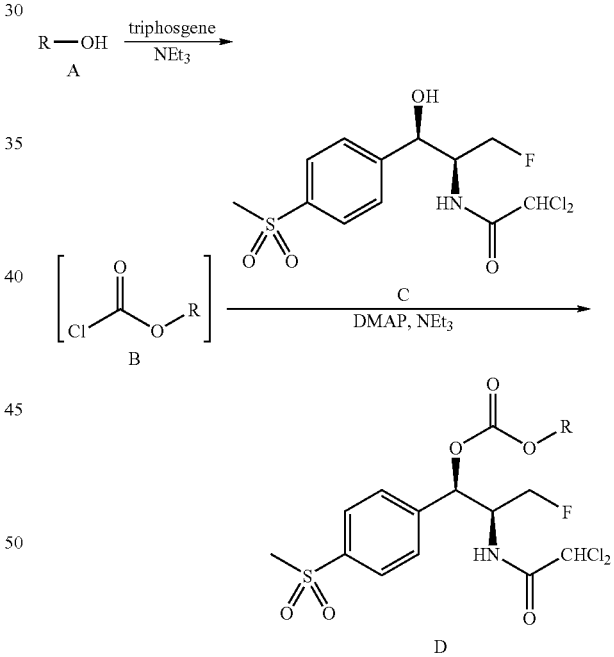

R = Boc protected terminal aminoalkyl

A solution of the starting alcohol A (1.78 molar equivalents) and triethylamine (1.78 molar equivalents) in anhydrous tetrahydrofuran (0.68 M was added dropwise to a solution of triphosgene (0.64 molar equivalents) in anhydrous tetrahydrofuran (0.48 M) at 0° C. under a nitrogen atmosphere. The resulting mixture was stirred at 0° C. for 30 minutes and then rapidly filtered through a filter paper to remove the ammonium salt. The filtrate of the chloroformate solution B was used for the following carbonation reaction without further purification.

The freshly prepared chloroformate solution of B, or an anhydrous tetrahydrofuran solution of the commercially available chloroformate B (1.78 molar equivalent, 0.34 M), was placed in a dropping funnel and ⅔ of the solution was added dropwise to an anhydrous tetrahydrofuran solution containing florfenicol C (1 molar equivalent, 0.64 M), 4-N,N-dimethylaminopyridine (DMAP, 0.5 molar equivalent), and triethylamine (1.5 molar equivalents) at 0° C. under a nitrogen atmosphere. The mixture was stirred at 0° C. for 30 minutes, and the progress of the reaction was monitored by thin layer chromatography. (If the reaction was not complete as indicated by the thin layer chromatography additional amount of chloroformate solution was added). The resulting solution was rapidly filtered through a filter paper to remove the ammonium salt. The filtrate was concentrated and ethyl acetate was added to dissolve the crude product. The resulting solution was washed sequentially with 1 M $HCl_{(aq)}$ saturated $NaHCO_{3(aq)}$, and saturated $NaCl_{(aq)}$, followed by a rapid filtration through a pad of silica gel and $Na_2SO_4$. The filtrate was concentrated and the crude product obtained was purified by flash column chromatography or recrystallization to give the desired protected carbonate D.

General Procedure II
Preparation of Florfenicol Esters

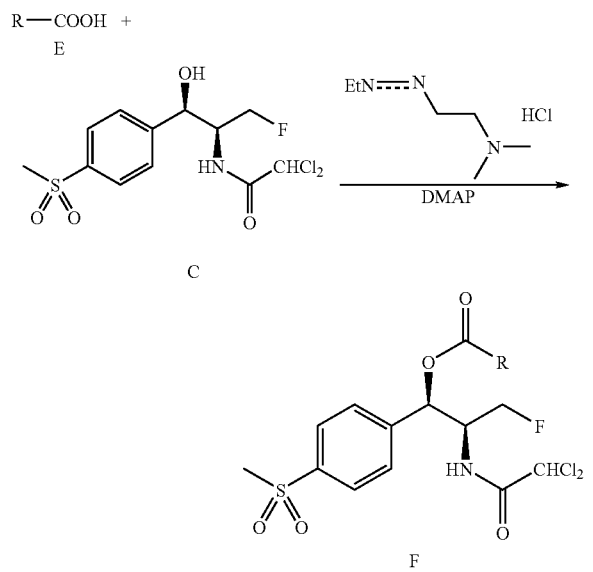

R = Boc protected terminal aminoalkyl

A solution of N-Boc protected terminal aminoalkyl carboxylic acid E (1.1 molar equivalents), florfenicol C (1.0 molar equivalent), N-(3-Dimethylaminopropyl)-N'-ethylcarbodiimide hydrochloride (2.0 equivalents), and 4-N/N-dimethylaminopyridine (0.5 molar equivalent) were mixed and stirred in anhydrous N,N-dimethylformamide (0.24 M) at room temperature under a nitrogen atmosphere overnight. The resulting solution was diluted with ethyl acetate and washed sequentially with 1 M $HCl_{(aq)}$, saturated $NaHCO_{3(aq)}$, and saturated $NaCl_{(aq)}$, followed by a rapid filtration through a pad of silica gel and $Na_2SO_4$. The filtrate was concentrated and the crude product obtained was purified by flash column chromatography to give desired ester D.

General Procedure III
Deprotection of Boc Protected Intermediates.

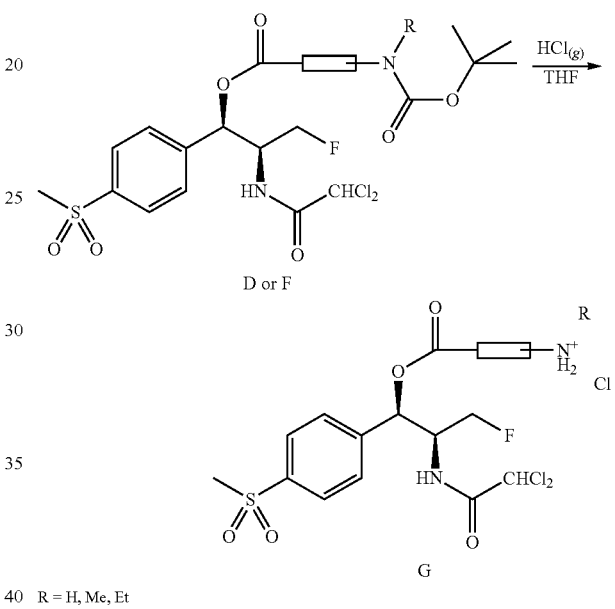

R = H, Me, Et

A solution of carbonate D (or ester F) in anhydrous tetrahydrofuran (0.14 M) was saturated with $HCl_{(g)}$ at 0° C. The resulting solution was stirred at room temperature for 30 minutes to 1 hour and purged with nitrogen to remove excess HCl. The solution was concentrated to dryness and the resulting solid material was dried under vacuum to give the desired amine hydrochloride product G.

General Procedure IV

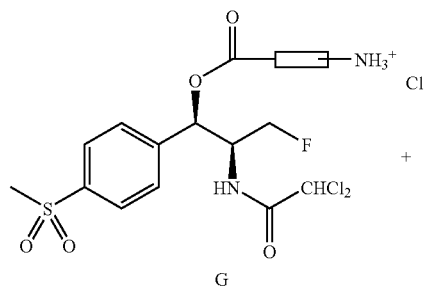

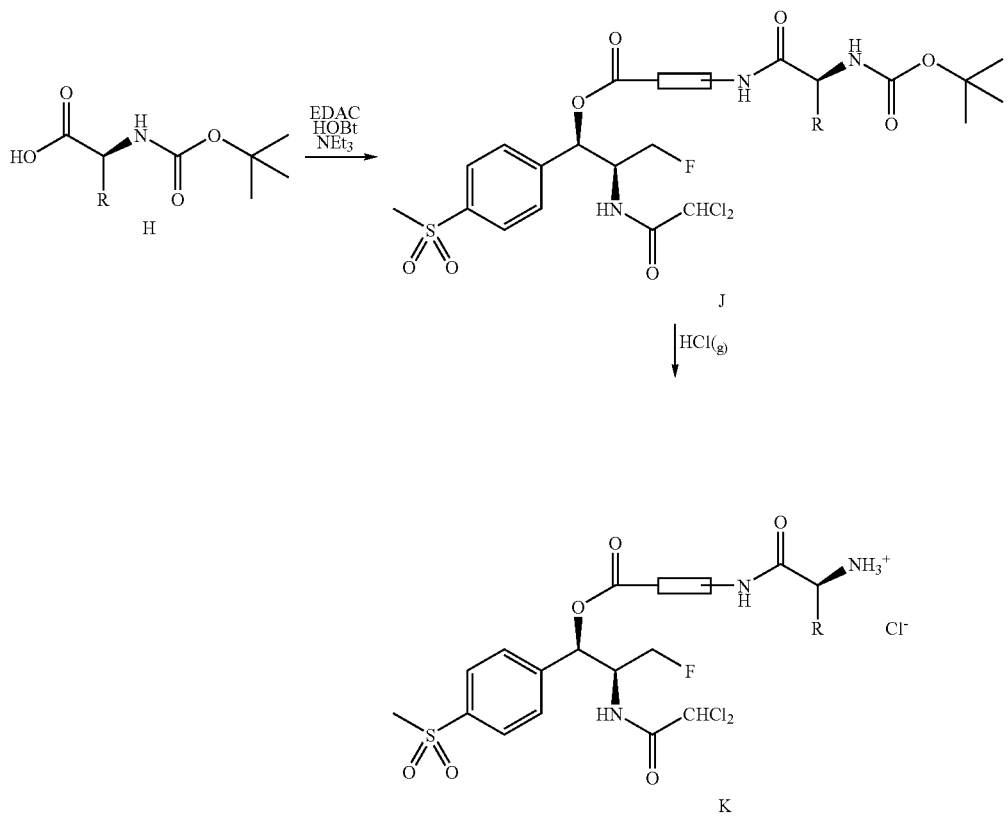

R = CH₂ or CH(CH₃)₂

A solution of G (1.0 equivalent) and triethylamine (1.0 equivalent) in anhydrous N,N-dimethylformamide (0.38 M) was stirred at room temperature under nitrogen atmosphere for 15 minutes. Sequential addition of Boc protected amino acid H (1.03 equivalents), N-(3-Dimethylaminopropyl)-N'-ethylcarbodiimide hydrochloride (EDAC, 2.0 equivalents), and 1-hydroxybezotriazole (HOBt, 0.5 equivalent) was carried out at room temperature. The final solution was stirred under nitrogen atmosphere at room temperature overnight and diluted with ethyl acetate. The resulting solution was washed sequentially with 1 M HCl$_{(aq)}$, saturated NaHCO$_{3(aq)}$, and saturated NaCl$_{(aq)}$, followed by a rapid filtration through a pad of silica gel and Na$_2$SO$_4$. The filtrate was concentrated and the crude product obtained was purified by flash column chromatography to give the pure product J.

A solution of J in anhydrous tetrahydrofuran (0.14 M) was saturated with HCl$_{(g)}$ at 0° C. The resulting solution was stirred at room temperature for 30 minutes to 1 hour and purged with nitrogen to remove excess HCl. The solution was concentrated to dryness and the resulting solid material was dried under vacuum to give the desired amine hydrochloride product K.

EXAMPLES

The following are representative examples of preparation of compounds according to the invention.

Example 1

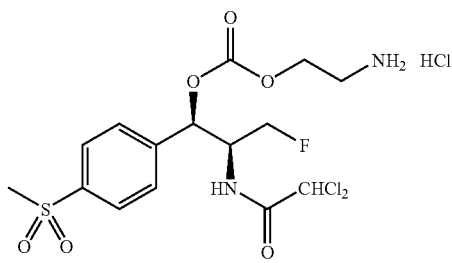

(1R,2S)-2-(2,2-dichloroacetamido)-3-fluoro-1-(4-(methylsulfonyl)phenyl)propyl 2-aminoethyl carbonate hydrochloride The title hydrochloride was obtained by general procedures I and III from 20 g of florfenicol and purified by stirring the solids in a mixture of ethyl acetate and hexanes overnight to give 28 g (quantitative yield) of a white powder. $H^1$-NMR (DMSO-$d_6$), δ=3.1 ppm (t, 2H), 3.2 ppm (s, 3H), 4.3 ppm (m, 2H), 4.4-4.7 (m, 3H), 5.9 ppm (d, 1H), 6.6 ppm (s, 1H), 7.6 ppm (d, 2H), 7.9 ppm (d, 2H), 8.2 ppm (br, 3H), 9.2 (d, 1H).

Example 2

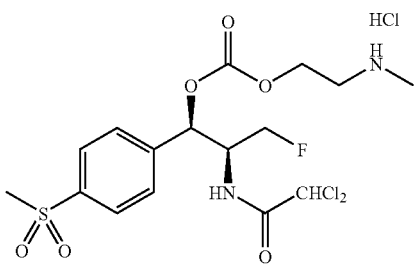

(1R,2S)-2-(2,2-dichloroacetamido)-3-fluoro-1-(4-(methylsulfonyl)phenyl)propyl 2-(methylamino) ethyl carbonate hydrochloride The title hydrochloride was obtained by general procedures I and III from 20 g of florfenicol without further purification to give 25 g (91% yield) of a white powder. $H^1$-NMR (DMSO-$d_6$), δ=2.5 ppm (s, 3H), 3.2 ppm (s, 5H), 4.3 ppm (m, 2H), 4.3-4.7 (m, 5H), 5.9 ppm (d, 1H), 6.6 ppm (s, 1H), 7.6 ppm (d, 2H), 7.9 ppm (d, 2H), 9.1 ppm (br, 2H), 9.3 (d, 1H).

Example 3

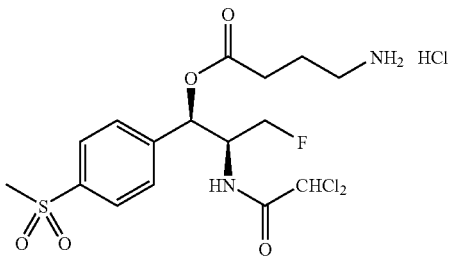

(1R,2S)-2-(2,2-dichloroacetamido)-3-fluoro-1-(4-(methylsulfonyl)phenyl)propyl 4-aminobutyrate hydrochloride The title hydrochloride was obtained by general procedures II and III from 9 g of florfenicol and dried at 65° C. under reduced pressure for 2 days to give 7 g (56% yield) of a white powder. $H^1$-NMR (DMSO-$d_6$), δ=1.8 ppm (p, 2H), 2.5 ppm (t, 2H), 2.8 ppm (t, 2H), 3.2 ppm (s, 3H), 4.3-4.7 (m, 3H), 6.0 ppm (d, 1H), 6.6 ppm (s, 1H), 7.6 ppm (d, 2H), 7.9 ppm (d, 2H), 8.1 ppm (br, 3H), 9.2 (d, 1H).

Example 4

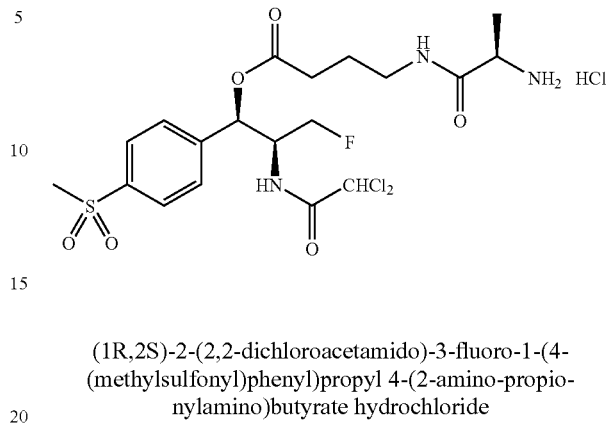

(1R,2S)-2-(2,2-dichloroacetamido)-3-fluoro-1-(4-(methylsulfonyl)phenyl)propyl 4-(2-amino-propionylamino)butyrate hydrochloride A solution of triethylamine (3.1 mL, 1.1 equivalent) and methyl 4-aminobutyrate hydrochloride (3.2 g, 1.05 equivalent) in 25 ml of anhydrous N,N-dimethylformamide was stirred at −10° C. under $N_2$ atmosphere for 10 minutes. Sequential addition of Boc-L-alanine (3.8 g, 1.0 equivalent), N-dimethylaminopropyl)-N'-ethylcarbodiimide hydrochloride (4.2 g, 1.1 equivalents), 1-hydroxybezotriazole (1.8 g, 0.6 equivalent), and 15 mL of anhydrous N,N-dimethylformamide was carried out at the same temperature. The final solution was stirred under $N_2$ atmosphere at room temperature overnight and diluted with ethyl acetate. The resulting solution was washed sequentially with 1 M $HCl_{(aq)}$, saturated $NaHCO_{3(aq)}$, and saturated $NaCl_{(aq)}$, followed by a rapid filtration through a pad of silica gel and $Na_2SO_4$. The filtrate was concentrated and dried under reduced pressure to give a crude paste (4.8 g). The paste was stirred in a mixture of 50 mL of tetrahydrofuran, 25 mL of methanol, and 20 mL of water with the presence of LiOH (0.45 g, 1.1 equivalents) for 1 hour at room temperature. The solution was acidified with concentrated HCl and extracted with ethyl acetate. The organic extracts were combined and washed with saturated $NaCl_{(aq)}$ and rapidly filtered through a pad of silica gel and $Na_2SO_4$. The filtrate was concentrated and dried under reduced pressure to give 4-(2-t-butoxycarbonylamino-propionylamino)butyric acid as a paste (4.0 g, 72% yield); $H^1$-NMR (DMSO-$d_6$), δ=1.1 ppm (d, 3H), 1.3 ppm (s, 9H), 1.6 ppm (p, 2H), 2.2 ppm (t, 2H), 3.0 ppm (m, 2H), 3.8 ppm (m, 1H), 6.8 ppm (d, 1H), 7.8 ppm (t, 1H).

The paste was utilized in the general procedure II as the starting acid A to give the product D as a white solid (6.2 g, 71% yield); $H^1$-NMR (DMSO-$d_6$) δ=1.1 ppm (d, 3H), 1.3 ppm (s, 9H), 1.6 ppm (p, 2H), 2.4 ppm (t, 2H), 3.0 ppm (m, 2H), 3.2 ppm (s, 3H), 3.8 ppm (m, 1H), 4.2-4.6 ppm (m, 3H), 6.0 ppm (d, 1H), 6.4 ppm (s, 1H), 6.9 ppm (d, 1H), 7.6 ppm (d, 2H), 7.8 ppm (t, 1H), 7.9 ppm (d, 2H), 8.9 ppm (d, 1H).

The solids were deprotected by following the general procedure III to give the prodrug in its free amino form as a white foam (2.4 g, 43% yield), after purification by gel column chromatography. $H^1$-NMR (DMSO-$d_6$), δ=1.3 ppm (d, 3H), 1.7 ppm (p, 2H), 2.4 ppm (t, 2H), 3.1-3.2 ppm (m, 7H), 3.7 ppm (q, 1H), 4.3-4.6 ppm (m, 3H), 6.0 ppm (d, 1H), 6.7 ppm (s, 1H), 7.6 ppm (d, 2H), 7.9 ppm (d, 2H), 8.5 ppm (t, 1H), 9.2 (d, 1H). The hydrochloride salt was prepared as described in General procedure III

Example 5

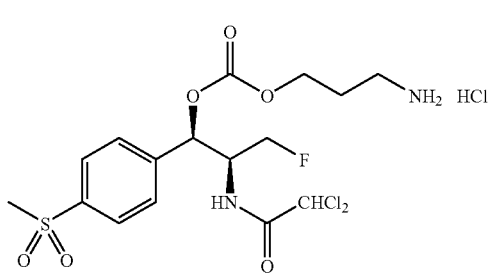

(1R,2S)-2-(2,2-dichloroacetamido)-3-fluoro-1-(4-(methylsulfonyl)phenyl)propyl 3-aminopropyl carbonate hydrochloride The title hydrochloride was obtained by general procedures I and III from 28 g of florfenicol and purified by stirring the crude solids in ether overnight to give 33 g (83% yield) of a white powder. $H^1$-NMR (DMSO-$d_6$), δ=1.9 ppm (p, 2H), 2.8 ppm (s, 2H), 3.2 ppm (s, 3H), 4.1 ppm (m, 2H), 4.3-4.7 (m, 3H), 5.9 ppm (d, 1H), 6.6 ppm (s, 1H), 7.6 ppm (d, 2H), 7.9 ppm (d, 2H), 8.1 ppm (br, 3H), 9.2 (d, 1H)

Example 6

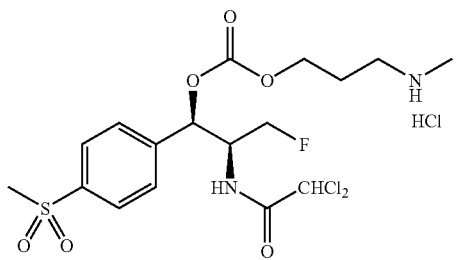

(1R,2S)-2-(2,2-dichloroacetamido)-3-fluoro-1-(4-(methylsulfonyl)phenyl)propyl 3-(methylamino)propyl carbonate hydrochloride The title hydrochloride was obtained by general procedures I and III from 2.8 g of florfenicol and purified by stirring the crude solids in a mixture of tetrahydrofuran and ether for 2 days to give 2.1 g (63% yield) of a white powder. $H^1$-NMR (DMSO-$d_6$), δ=1.9 ppm (p, 2H), 2.9 ppm (t, 2H), 3.2 ppm (s, 3H), 4.1 ppm (t, 2H), 4.3-4.7 ppm (m, 3H), 5.9 ppm (d, 1H), 6.6 ppm (s, 1H), 7.6 ppm (d, 2H), 7.9 ppm (d, 2H), 8.9 ppm (br, 2H), 9.2 (d, 1H).

Example 7

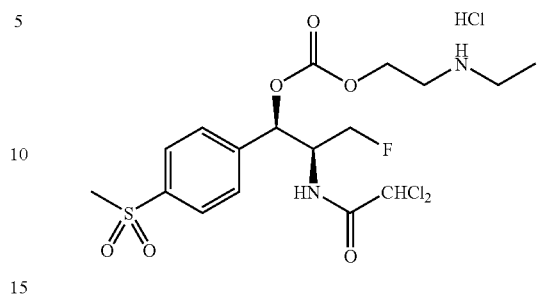

(1R,2S)-2-(2,2-dichloroacetamido)-3-fluoro-1-(4-(methylsulfonyl)phenyl)propyl 2-(ethylamino)ethyl carbonate hydrochloride Upon stirring a solution of di-t-butyl dicarbonate (24.5 g) in 50 mL of tetrahydrofuran at −10° C., 2-(ethylamino)ethanol (11 mL) and triethylamine (16 mL) were added sequentially. The solution was stirred at room temperature for 1.5 hours, diluted with ethyl acetate, washed sequentially with 1 M $HCl_{(aq)}$ and saturated $NaCl_{(aq)}$. The organic layer was separated and rapidly filtered through a pad of silica gel and sodium sulfate. The filtrate was concentrated and the crude product was dried under reduced pressure to give ethyl-(2-hydroxy-ethyl)-carbamic acid t-butyl ester as a pale oil (21 g, 99% yield); $H^1$-NMR (CDCl$_3$), δ=1.1 ppm (t, 3H), 1.4 ppm (s, 9H), 2.7 ppm (s, 1H), 3.2 ppm (q, 2H), 3.4 ppm (t, 2H), 3.7 ppm (t, 2H).

The crude material (10 g) was utilized in the general procedure I as the starting alcohol A to give the product D as a white foam (14.7 g, 97% yield); $H^1$-NMR (DMSO-$d_6$), δ=1.0 ppm (br, 3H), 1.4 ppm (s, 9H), 3.1 ppm (q, 2H), 3.2 ppm (s, 3H), 3.4 ppm (m, 2H), 4.2 ppm (t, 2H), 4.3-4.7 (m, 5H), 5.9 ppm (d, 1H), 6.4 ppm (s, 1H), 7.6 ppm (d, 2H), 7.9 ppm (d, 2H), 9.0 ppm (d, 2H).

The intermediate obtained above was deprotected by following the general procedure III to give the title hydrochloride (11 g, 84% yield) as a white powder after the crude solids were purified by being stirred in a mixture of 100 mL tetrahydrofuran and 20 mL of ether for 1 hour, isolated by filtration, and dried under reduced pressure. $H^1$-NMR (DMSO-$d_6$), δ=1.2 ppm (t, 3H), 2.9 ppm (q, 2H), 3.2 ppm (s, 5H), 4.3-4.7 (m, 5H), 5.9 ppm (d, 1H), 6.6 ppm (s, 1H), 7.6 ppm (d, 2H), 7.9 ppm (d, 2H), 8.9 ppm (br, 2H), 9.2 (d, 1H).

Example 8

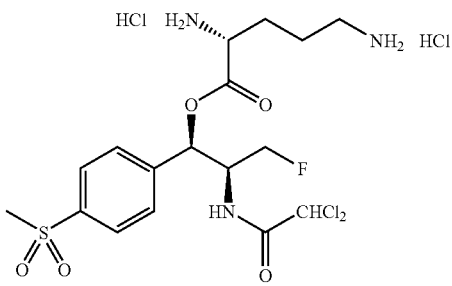

((1R,2S)-2-(2,2-dichloroacetamido)-3-fluoro-1-(4-(methylsulfonyl)phenyl)propyl 1,4-diaminopentanoate dihydrochloride Thionyl chloride (2.8 mL, 1.3 equivalents) was added in several portions to a mixture of L-ornithine hydrochloride (5 g, 1 equivalent) in 50 mL of methanol at −10° C. under a nitrogen atmosphere. The resulting solution was stirred at room temperature for 1 hour and the solvent was removed to give the methyl ester derivative as white foam (6.7 g). The foam was stirred in a mixture of tetrahydrofuran and methanol (50 mL/50 mL) with the presence of triethylamine (12 mL, 3 equivalents) for 20 minutes at room temperature, followed by the addition of di-t-butyl dicarbonate (12.5 g, 2 equivalents) into the mixture. The resulting solution was stirred at room temperature overnight and then filtered through a filter paper to remove the ammonium salt. The filtrate was concentrated and the solids obtained were dissolved in ethyl acetate and washed sequentially with 1 M $HCl_{(aq)}$ and saturated $NaCl_{(aq)}$. The organic portion was rapidly filtered through a pad of silica gel and sodium sulfate. The filtrate was concentrated to give a crude paste which was allowed to be stirred in a mixture of tetrahydrofuran (50 mL) and 2N $NaOH_{(aq)}$ (13 mL) at room temperature for 10 minutes. The solution was acidified with 1 M $HCl_{(aq)}$ and extracted with ethyl acetate. The organic layer was separated and rapidly filtered through a pad of silica gel and sodium sulfate. The filtrate was concentrated and dried under reduced pressure to give 2,5-bis-t-butoxycarbonylamino-pentanoic acid as a white foam (8.8 g, 83% yield); $H^1$-NMR (DMSO-$d_6$), δ=1.3-1.8 ppm (m, 22H), 2.9 ppm (q, 2H), 3.9 ppm (m, 1H), 6.8 ppm (br, 1H), 7.0 ppm (d, 0.6H), 7.2 ppm (d, 0.4H).

This protected ornithine intermediate obtained above was utilized as the starting acid A in the general procedure II to give the product D as a white foam (8.7 g, 71% yield); $H^1$-NMR (DMSO-$d_6$), δ=1.3-1.8 ppm (m, 22H), 2.9 ppm (br, 2H), 3.2 ppm (s, 3H), 4.0-4.7 ppm (m, 4H), 6.0 ppm (s, 1H), 6.4 PPM (S, 1H), 6.8 ppm (br, 1H), 7.3 ppm (d, 4H), 7.6 ppm (d, 2H), 7.9 ppm (d, 2H), 8.9 ppm (d, 2H).

The intermediate obtained above was deprotected by following the general procedure III to give the title hydrochloride as white solids (6.8 g 97% yield) without further purification; $H^1$-NMR (DMSO-$d_6$), δ=1.8-2.2 ppm (m, 2H), 2.8 ppm (br, 2H), 3.2 ppm (s, 3H), 3.6 ppm (m, 2H), 4.2-4.7 ppm (m, 4H), 6.2 ppm (s, 1H), 6.9 ppm (s, 1H), 7.7 ppm (d, 2H), 7.9 ppm (d, 2H), 8.0 ppm (br, 3H), 8.8 ppm (br, 3H), 9.6 ppm (d, 1H).

Example 9

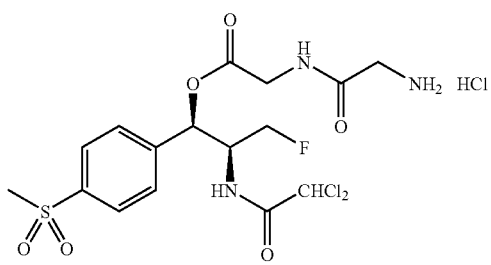

(1R,2S)-2-(2,2-dichloroacetamido)-3-fluoro-1-(4-(methylsulfonyl)phenyl)propyl (1-amino-acetoamino)acetate hydrochloride By following the general procedures II, III, and IV using 24 g of florfenicol and 12 g of N-Boc-glycine, the title hydrochloride (20 g, 56% yield) was obtained as white powder after the crude solids were purified by being stirred in 200 mL of warm dichloromethane for 20 minutes, isolated by filtration, and dried under reduced pressure at 50° C. for 6 days; $H^1$-NMR (DMSO-$d_6$), δ=3.2 ppm (m, 3H), 3.6 ppm (s, 2H), 4.1 ppm (d, 2H), 4.3-4.7 ppm (m, 3H), 6.0 ppm (s, 1H), 6.7 ppm (s, 1H), 7.6 ppm (d, 2H), 7.9 ppm (d, 2H), 8.1 ppm (br, 3H), 9.0 ppm (t, 1H), 9.2 ppm (d, 1H).

Example 10

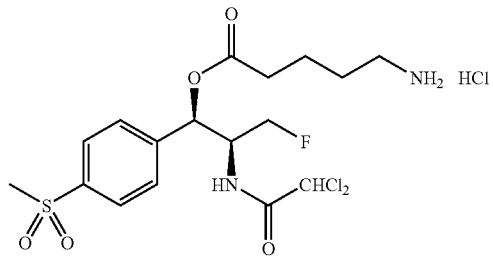

(1R,2S)-2-(2,2-dichloroacetamido)-3-fluoro-1-(4-(methylsulfonyl)phenyl)propyl 5-aminopentanoate hydrochloride The title hydrochloride was obtained by general procedures II and III from 8.2 g of florfenicol and 5-t-butoxycarbonylamino-pentanoic acid and purified by stirring the crude solids in a mixture of tetrahydrofuran for 2 days to give a white powder (6.2 g, 96% yield). $H^1$-NMR (DMSO-$d_6$), δ=1.5 ppm (m, 4H), 2.4 ppm (m, 2H), 2.7 ppm (br, 2H), 3.2 ppm (s, 3H), 4.3-4.6 (m, 3H), 6.0 ppm (d, 1H), 6.6 ppm (s, 1H), 7.6 ppm (d, 2H), 7.9 ppm (m, 5H), 9.1 ppm (d, 1H).

Example 11

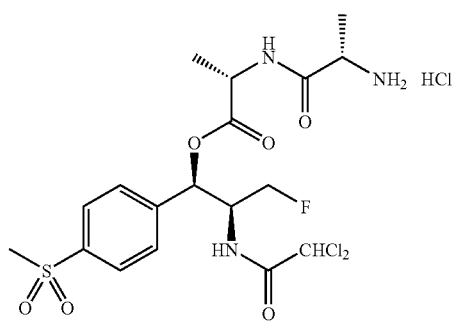

(1R,2S)-2-(2,2-dichloroacetamido)-3-fluoro-1-(4-(methylsulfonyl)phenyl)propyl 2-(2-amino-propionylamino)propionate hydrochloride By following the general procedures II, III, and IV using 9 g of florfenicol and 5.4 g of Boc-L-alanine, the title hydrochloride (5.2 g 58% yield) was obtained as a white powder after the crude solids were purified by a rapid precipitation from a mixture of dichloromethane and methanol, isolated by filtration, and dried under reduced pressure; H$^1$-NMR (DMSO-d$_6$), δ=1.4 ppm (d, 6H), 3.1 ppm (s, 3H), 3.9 ppm (q, 1H), 4.3-4.7 ppm (m, 4H), 6.0 ppm (s, 1H), 6.7 ppm (s, 1H), 7.6 ppm (d, 2H), 7.9 ppm (d, 2H), 8.2 ppm (br, 3H), 9.2 ppm (d, 1H), 9.3 ppm (d, 1H).

Example 12

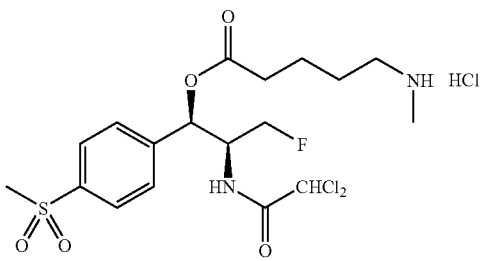

(1R,2S)-2-(2,2-dichloroacetamido-3-fluoro-1-(4-(methylsulfonyl)phenyl)propyl 5-(methylamino) pentanoate hydrochloride An ethanol solution (30 mL) of 1-methyl-2-piperidinone (5 g, 1 equivalent) and KOH (5.4 g, 2 equivalents) was heated at 90° C. overnight. After cooling the solution to room temperature, di-1-butyl dicarbonate (19.2 g, 2 equivalents) and 100 mL of ethanol were introduced. The resulting solution was stirred at room temperature for 30 minutes and filtered through a filter paper to remove the solids. The filtrated was concentrated and acidified with 1 M HCl$_{(aq)}$ and extracted with ethyl acetate. The organic extracts were combined, concentrated, and purified by gel column chromatography. Two fractions were obtained from the chromatography. The more polar fraction contained the desired 5-(t-butoxycarbonyl-methyl-amino)pentanoic acid and the less polar fraction obtained were hydrolyzed by NaOH$_{(aq)}$ to obtain more of the desired acid. The combined yield of the acid was 8.3 g (81%) as a brown paste; H$^1$-NMR (CDCl$_3$), δ=1.4 ppm (s, 9H), 1.6 ppm (m, 4H), 2.4 ppm (t, 2H), 2.8 ppm (s, 3H), 3.2 ppm (t, 3H).

This paste (3 g, 1.1 equivalents) was utilized as the starting acid A in the general procedure II to give the product D as white foam (6.5 g, 86% yield); H$^1$-NMR (DMSO-D$_6$), δ=1.3-1.5 ppm (m, 13H), 2.5 ppm (m, 2H), 2.7 ppm (s, 3H), 3.1-3.2 ppm (m, 5H), 4.2-4.6 ppm (m, 3H), 6.0 ppm (d, 1H), 6.4 ppm (s, 1H), 7.6 ppm (d, 2H), 7.9 ppm (d, 2H), 8.9 ppm (d, 2H).

The foam was deprotected by following the general procedure III to give the title hydrochloride as a yellow foam (6.1 g, quantitative yield) without further purification; H$^1$-NMR (DMSO-d$_6$), δ=1.6 ppm (br, 4H), 2.8 ppm (br, 2H), 3.2 ppm (s, 3H), 3.6 ppm (s, 5H), 4.2-4.6 ppm (m, 3H), 6.0 ppm (d, 1H), 6.6 ppm (s, 1H), 7.6 ppm (d, 2H), 7.9 ppm (d, 2H), 8.8 ppm (br, 2H), 9.2 ppm (d, 1H).

Example 13

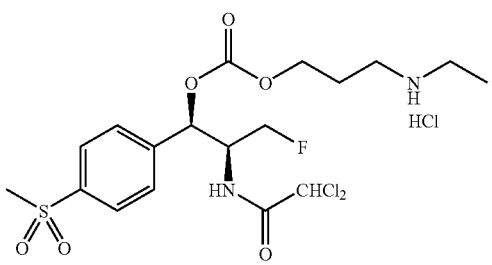

(1R,2S)-2-(2,2-dichloroacetamido)-3-fluoro-1-(4-(methylsulfonyl)phenyl)propyl 3-(ethylamino)propyl carbonate hydrochloride A mixture of 3-chloropropanol (4.4 mL, 1 equivalent) and ethylamine (15 mL, 3 equivalents) were heated in a sealed tube for 2 days. After cooling to room temperature, solid K$_2$CO$_3$ was added. After filtering off the solids the desired product was obtained as a crude paste after the removal of side products by distillation at 95° C. at reduced pressure. The residual paste was treated with di-t-butyl dicarbonate (12 g, 1 equivalent) while being stirred in methanol (50 mL) in the presence of triethylamine (16 mL, 2 equivalents). The solution was stirred at room temperature for 30 minutes, concentrated, and diluted with ethyl acetate. The organic solution was washed with 1 M HCl$_{(aq)}$ and saturated NaCl$_{(aq)}$. The organic layer was separated and concentrated to give a colorless crude oil which was purified by gel column chromatography to give ethyl-(3-hydroxy-propyl)-carbamic acid t-butyl ester as a colorless oil (10 g, 93% yield); H$^1$-NMR (CDCl$_3$), δ=1.1 ppm (t, 3H), 1.4 ppm (s, 9H), 1.7 ppm (p, 2H), 3.2 ppm (q, 2H), 3.4 ppm (t, 2H), 3.6 ppm (t, 2H).

The resulting oil was utilized as the starting alcohol A in the general procedure I to give the product 1) as a white foam (13.7 g, 95% yield); H$^1$-NMR (DMSO-d$_6$), δ=1.0 ppm (t, 3H), 1.3 ppm (s, 9H), 1.8 ppm (p, 2H), 3.0-3.2 ppm (m, 7H), 4.0 ppm (t, 2H), 4.3-4.7 ppm (m, 3H), 5.9 ppm (d, 1H), 6.4 ppm (s, 1H), 7.6 ppm (d, 2H), 7.9 ppm (d, 2H), 9.0 (d, 1H).

The foam was deprotected by following the general procedure III to give the title hydrochloride (11.9 g, 97% yield) as a white foam after the crude solids were purified by gel column chromatography; H$^1$-NMR (DMSO-d$_6$), δ=1.2 ppm (t, 3H), 1.9 ppm (m, 2H), 2.9 ppm (m, 4H), 3.2 ppm (s, 3H), 4.1-4.7 ppm (m, 5H), 5.9 ppm (d, 1H), 6.5 ppm (s, 1H), 7.6 ppm (d, 2H), 7.9 ppm (d, 2H), 8.9 ppm (br, 2H), 9.2 (d, 1H).

Example 14

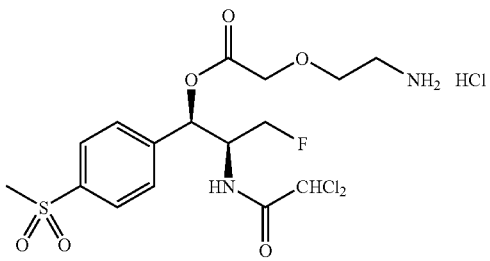

(1R,2S)-2-(2,2-dichloroacetamido)-3-fluoro-1-(4-(methylsulfonyl)phenyl)propyl (2-amino-ethoxy) acetate hydrochloride Upon stirring a solution of 2-aminoethanol (12 mL, 1.2 equivalents) and triethylamine (22 mL, 1 equivalent) in tetrahydrofuran (150 mL) at room temperature, di-t-butyl dicarbonate (35 g, 1 equivalent) was added in several portions. The solution was stirred at room temperature for 20 minutes, diluted with ethyl acetate, washed with 1 M $HCl_{(aq)}$ and saturated $NaCl_{(aq)}$. The organic layer was separated and rapidly filtered through a pad of silica gel and sodium sulfate. The filtrate was concentrated and the crude product t-butyl-N-(2-hydroxyethyl)carbamate (24 g, 92% yield) was obtained as colorless oil after drying under reduced pressure; $H^1$-NMR (DMSO-$d_6$), δ=1.3 ppm (s, 9H), 2.9 ppm (q, 2H), 3.3 ppm (q, 2H), 4.6 (t, 1H), 6.6 ppm (t, 1H).

The oil (13.3 g, 1 equivalent) was dissolved in tetrahydrofuran (150 mL) ad stirred at −78° C. while NaH (4.6 g, 1.4 equivalents) was added in several portions. The resulting mixture was stirred at room temperature for 1 hour and followed by the introduction of ethyl bromoacetate (12.7 ml, 1.4 equivalents) at −78° C. The mixture was stirred at room temperature overnight and diluted with ethyl acetate. The solution was washed with 1 M $HCl_{(aq)}$ and concentrated. The crude mixture obtained was purified by gel column chromatography to give the desired product ethyl 2-aminoethoxy-N-t-butoxycarbonylacetate (10 g, 50% yield) as a colorless oil; $H^1$-NMR (CDCl$_3$), δ=1.3 ppm (t, 3H), 1.4 ppm (s, 9H), 3.3 ppm (m, 2H), 3.6 ppm (t, 2H), 4.1 ppm (s, 2H), 4.2 ppm (q, 2H), 5.1 ppm (br, 1H).

The oil (5 g, 1 equivalent) was hydrolyzed with $NaOH_{(s)}$ (1 g, 1.2 equivalents) in a mixture of tetrahydrofuran (20 mL) and water (20 mL) at room temperature within 5 minutes. The mixture was extracted with ether to remove impurities, the resulting mixture was acidified with 6 N $HCl_{(aq)}$ and extracted with ethyl acetate. The combined extracts were washed with saturated $NaCl_{(aq)}$ and rapidly filtered through a pad of silica gel and sodium sulfate. The filtrate was concentrated and the desired (2-t-butoxycarbonylamino-ethoxy)acetic acid (4 g, 90% yield) was obtained as a colorless oil after drying under reduced pressure; $H^1$-NMR (DMSO-$d_6$), δ=1.3 ppm (s, 9H), 3.0 ppm (q, 2H), 3.4 ppm (t, 2H), 3.9 ppm (s, 2H), 6.6 ppm (t, 1H), 12.6 ppm (br, 1H).

The resulting material was utilized as the starting acid A in the general procedure II to give the product D (7.8 g, 84% yield) as a white foam; $H^1$-NMR (DMSO-$d_6$), δ=1.3 ppm (s, 9H), 3.1 ppm (q, 2H), 3.2 ppm (s, 3H), 3.4 ppm (t, 2H), 4.2-4.6 (m, 5H), 6.0 ppm (d, 1H), 6.4 ppm (s, 1H), 6.8 ppm (t, 1H), 7.6 ppm (d, 2H), 7.9 ppm (d, 2H), 8.9 ppm (d, 1H).

The foam (15.3 g) was deprotected by following the general procedure III to give the title hydrochloride (9.9 g, 74% yield) as a white powder after the crude product was extracted consecutively with warm tetrahydrofuran and warm dichloromethane and dried under reduced pressure at 50° C. for 2 days; $H^1$-NMR (DMSO-$d_6$), δ=2.9 ppm (br, 2H), 3.2 ppm (s, 3H), 3.7 ppm (t, 2H), 4.2-4.7 (m, 5H), 6.1 ppm (d, 1H), 6.6 ppm (s, 1H), 7.6 ppm (d, 2H), 7.9 ppm (d, 2H), 8.0 ppm (br, 3H), 9.2 ppm (d, 1H).

Example 15

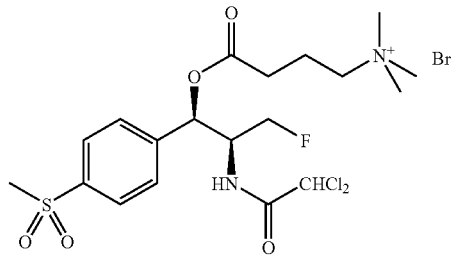

{3-[2-(2,2-Dichloro-acetylamino)-3-fluoro-1-(4-methanesulfonyl-phenyl)-propoxycarbonyl-propyl}-trimethyl-ammonium bromide Upon stirring a mixture of florfenicol (8.8 g, 1 equivalent), diisopropylethylamine (5 mL, 1.2 equivalents), and 4-N,N-dimethylaminopyridine (1.2 g, 0.4 equivalent) in tetrahydrofuran (90 mL) at −20° C., a solution of 4-bromobutyryl chloride (5 g, 1.1 equivalent) in tetrahydrofuran (15 mL) was added via a syringe. The solution was stirred at room temperature under a nitrogen atmosphere overnight and diluted with ethyl acetate. The resulting solution was washed with 1 M $HCl_{(aq)}$ and the organic layer was separated and concentrated to give a brown oil. The crude oil was purified by gel column chromatography to give 4-bromo-butyric acid 2-(2,2-dichloro-acetyl amino)-3-fluoro-1-(4-methanesulfonyl-phenyl)-propyl ester (5.6 g, 45% yield) as a brown foam; $H^1$-NMR (DMSO-$d_6$), δ=2.1 ppm (p, 2H), 2.6 ppm (t, 2H), 3.2 ppm (s, 3H), 3.5 ppm (t, 2H), 4.2-4.6 (m, 3H), 6.0 ppm (d, 1H), 6.4 ppm (s, 1H), 7.6 ppm (d, 2H), 7.9 ppm (d, 2H), 8.9 ppm (d, 2H).

A solution of the ester (1.1 g, 1 equivalent) in tetrahydrofuran (2 mL) was stirred at −78° C. while neat trimethylamine (0.4 mL, 2 equivalents) was added. The resulting solution was stirred at room temperature in a sealed tube overnight. The precipitates were collected by filtration and stirred in dichloromethane at room temperature for 24 hours. The purified title ammonium bromide was collected by filtration and dried under reduced pressure at 50° C. for 2 days to give a pale powder (0.8 g 65% yield); $H^1$-NMR (CDCl$_3$/CD$_3$OD), δ=2.0 ppm (m, 2H), 2.6 ppm (m, 2H), 3.0 ppm (s, 3H), 3.1 ppm (s, 9H), 3.4-3.6 ppm (m, 3H), 4.2-4.4 ppm (m, 3H), 6.0 ppm (d, 1H), 6.4 ppm (s, 1H), 7.6 ppm (d, 2H), 7.8 ppm (d, 2H).

Example 16

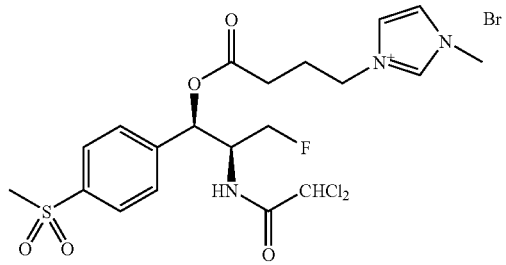

1-[3-[2-(2,2-Dichloro-acetylamino)-3-fluoro-1-(4-methanesulfonyl-phenyl)-propoxycarbonyl]-propyl]-3-methyl-3H-imidazol-1-ium bromide A solution of 4-bromo-butyric acid 2-(2,2-dichloro-acetylamino)-3-fluoro-1-(4-methanesulfonyl-phenyl)-propyl ester (1.8 g, 1 equivalent) and 1-methylimidazol (0.56 mL, 2 equivalents) was stirred in tetrahydrofuran (6 mL) at room temperature overnight. The solution was diluted with ether and the precipitates were collected by filtration and stirred in a mixture of ethyl acetate and hexanes (1:1) at room temperature for 24 hours. The purified title methylimidazolium bromide was collected by filtration and dried under reduced pressure at 50° C. for 7 hours to give a pale powder (1.2 g, 56% yield); $H^1$-NMR (CDCl$_3$/CD$_3$OD). δ=2.2 ppm (m, 2H), 2.6 ppm (m, 2H), 3.0 ppm (s, 3H), 3.9 ppm (s, 3H), 4.2-4.5 ppm (m, 5H), 6.0 ppm (d, 1H), 6.4 ppm (s, 1H), 7.2 ppm (d, 1H), 7.4 ppm (s, 1H), 7.6 (d, 2H), 7.8 ppm (d, 2H), 9.4 ppm (s, 1H).

Example 17

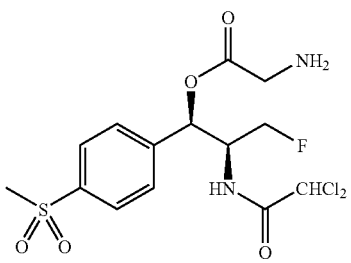

Amino-acetic acid 2-(2,2-dichloro-acetylamino)-3-fluoro-1-(4-methanesulfonyl-phenyl)-propyl ester By following the general procedures II and III using 12.9 g of florfenicol and 6.9 g of N-Boc glycine, the prodrug (13.2 g, 80% yield) was obtained as white powder after the crude solids were dried under reduced pressure at 50° C. for 6 days; $H^1$-NMR (DMSO-d$_6$), δ=3.2 ppm (m, 3H), 3.9 ppm (s, 2H), 4.3-4.7 ppm (m, 3H), 6.1 ppm (s, 1H), 6.8 ppm (s, 1H), 7.7 ppm (d, 2H), 7.9 ppm (d, 2H), 8.6 ppm (br, 3H), 9.4 ppm (d, 1H).

The following examples demonstrate the activity and effect of compounds of the invention.

Compounds of Table 1 were tested for stability in aqueous solutions and stability in bovine or porcine sera as follows:

Determination of stability of prodrugs in aqueous solutions.

at pH 7.4

Prodrugs were dissolved in pH 7.4 phosphate buffer at concentration of 1 mg/mL.

The clear solution was placed at room temperature. 400 μL aliquots of the solution were transferred at times 0, 1, 2, 8, 24, and 48 hours to plastic tubes containing 400 μL dilute HCl solution to achieve the final pH of around 4.0. Samples were analyzed by HPLC. The peak area of florfenicol was used to determine the rate of the parent drug release.

at pH 4.5

Prodrugs were dissolved in distilled water at concentration of 0.5 mg/mL. The pH was adjusted to 4.5 with dilute HCl when necessary. The clear solution was placed at room temperature. Samples for analysis were removed at times 0, 1, 2, 4, and 7 days. Samples were analyzed by HPLC. Peak area of florfenicol was used to determine the rate of the parent drug release.

Determination of stability of prodrugs in bovine or swine serum;

10 mg/mL in dimethylsulfoxide stock solutions of prodrugs were prepared. 50 μL of the above stock solution was added to 5 mL bovine or swine serum, and mixed. 400 μL aliquots of the above pro-drug serum solutions were transferred into plastic tubes (one tube per time point). Solutions were incubated at 37° C. for predetermined time. Samples were removed at times 0, 1, 2, 4, 8, and 24 hours and were spiked with 400 μL of acetonitrile. Samples were stirred for 30 seconds to precipitate the protein and to stop the reaction and were centrifuged at 14,000 rpm for 5 minutes. The supernatant was collected for HPLC analysis. Peak area of florfenicol was used to determine the rate of the parent drug release HPLC Conditions Instrument: Agilent 1100

Column: C18, 5 mm, 2.1 mm×150 mm

Flow rate: 0.5 mL/min

Temperature: 30° C.

Detector: UV 254 nm

Injection volume: 10 mL

Solvent: gradient with 0.1% formic acid in water, acetonitrile

Results are shown in Table 2.

TABLE 2

| Compound of example No. | Half life | | | | Comments |
| | pH 4.5 (days) | pH 7.4 (hours) | Bovine serum (hours) | Swine serum (hours) | |
| --- | --- | --- | --- | --- | --- |
| 1 | 202 | 1.8 | 0.7 | | Carbonate prodrug; formation of prodrug isomer in both pH 7.4 buffer and bovine serum |
| 2 | 487 | 0.5 | — | | Carbonate prodrug; formation of prodrug isomer in both pH 7.4 buffer and bovine serum |
| 3 | No observable degradation | 300 | 3.5 | | |
| 4 | 278 | 670 | 6.5 | | |
| 5 | 248 | 83 | 3.8 | 9.5 | Carbonate prodrug; no prodrug isomer formation |

TABLE 2-continued

| Compound of example No. | Half life pH 4.5 (days) | pH 7.4 (hours) | Bovine serum (hours) | Swine serum (hours) | Comments |
|---|---|---|---|---|---|
| 6 | 269 | 74 | 0.69 | 7.0 | Carbonate prodrug; formation of v. small amount prodrug isomer in pH 7.4 buffer; no isomer in bovine serum |
| 7 | 156 | 6.1 | 0.59 | | Carbonate prodrug; formation of prodrug isomer in pH 7.4 buffer; no isomer in bovine serum |
| 8 | 44 | <10 min | <10 min | | |
| 9 | 52 | 0.89 | 1.4 | 1.2 | |
| 10 | 643 | 100 | 0.49 | 4.1 | |
| 11 | 290 | 2.5 | <10 min | | |
| 12 | 567 | 84 | 1.4 | | |
| 13 | 339 | 290 | 0.71 | | Carbonate prodrug; no prodrug isomer formation |
| 14 | 137 | 0.66 | <10 min | | |
| 15 | >1000 | 160 | — | | |
| 16 | >1000 | 350 | 10.5 | — | |
| 17 | 18 | 4.4 | 1.8 | — | |

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding it will be readily apparent to those of ordinary skill in the art in light of the teachings of this invention that certain changes and modifications may be made thereto without departing from the spirit or scope of the appended claims.

What is claimed is:

1. A compound having the Formula (I)

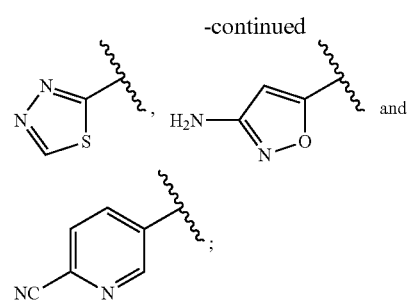

in which:
R is selected from the group consisting of

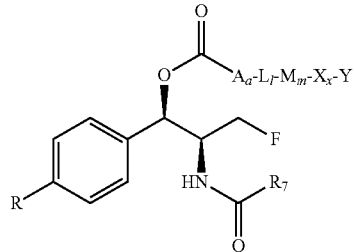

-continued

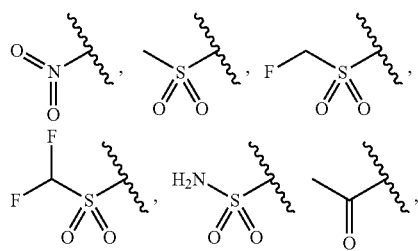

A is oxygen and a is zero or 1;

L is (a) $CH_2$ and l is an integer from 1 to 6; (b) $CHR_1$ where $R_1$ is an amino acid side chain and l is 1; or (c) $CHR_1NHC(O)CH(NH_2)R_2$ where $R_1$ and $R_2$ are amino acid side chains and l is 1;

M is (a) oxygen or sulfur and m is zero or one; (b) $CH_2$ and m is zero or an integer from 1 to 4; or (c) NH and m is 1;

X is (a) $CH_2$ and x is zero or an integer from 1 to 4; or (b) C(O) and x is 1; and Y is (a) $NH_2$; (b) $NHR_x$ where $R_x$ is methyl, ethyl, n-propyl or isopropyl; (c) $NR_yR_z$ where $R_y$ and $R_z$ are independently hydrogen, methyl, ethyl, n-propyl or isopropyl, or $R_y$ and $R_z$ taken together form a $C_2$-$C_5$ alkylene chain, or a $C_2$-$C_4$ alkylene chain further including a nitrogen or oxygen heteroatom in said chain; (d) $C(=NH)NH_2$; (e) $N^+R_4R_5R_6$ where $R_4$, $R_5$ and $R_6$ are independently hydrogen, methyl or ethyl, or $R_4$ and $R_5$ taken together form a $C_2$-$C_5$ alkylene chain, or a $C_2$-$C_4$ alkylene chain further including a nitrogen or oxygen heteroatom in said chain; (f) pyridinium; (g) N-methyl or N-ethyl pyridinium; (h) N'-3-methyl-N-1-imidazolium; (i) a phenyl group substituted by a group having the formula $NR_4R_5$ or $N^+R_4R_5R_6$ where $R_4$, $R_5$ and $R_6$ are as defined above; or (j) $NH-CR_3(=NH)$ where $R_3$ is hydrogen, methyl or amino;

and $R_7$ is selected from the group consisting of dichloromethyl, difluoromethyl, trifluoromethyl, cyanomethyl, azidomethyl, and aminomethyl;

provided that the group $A_aL_lM_mX_xY$ is other than an alpha-N-unfunctionalized glycine, ornithine or lysine residue;

and provided that when a is 0; one or more L, M or X are CH$_2$; and Y is NH$_2$; the sum of l, m, and x is 2-6;
and pharmaceutically acceptable salts thereof.

2. A compound having the Formula (II):

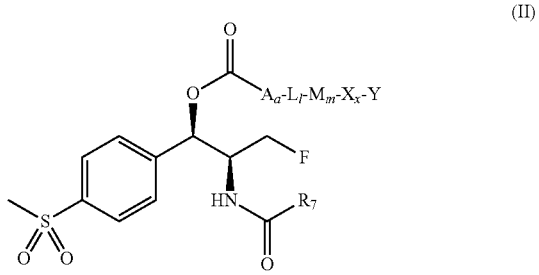

in which:
A is oxygen and a is zero or 1;
L is (a) CH$_2$ and l is an integer from 1 to 5 or (b) CHR$_1$ where R$_1$ is an amino acid side chain and l is 1; or (c) CHR$_1$NHC(O)CH(NH$_2$)R$_2$ where R$_2$ is an amino acid side chain and l is 1;
M is (a) oxygen and m is zero or one; (b) CH$_2$ and m is zero or an integer from 1 to 4; or (c) NH and m is 1;
X is (a) CH$_2$ and x is zero or an integer from 1 to 4; or (b) C(O) and x is 1; and
Y is (a) NH$_2$; (b) NHR$_x$ where R$_x$ is methyl, ethyl, n-propyl or isopropyl; (c) NR$_y$R$_z$ where R$_y$ and R$_z$ are independently hydrogen, methyl, ethyl, n-propyl or isopropyl; (d) C(=NH)NH$_2$; (e) N$^+$R$_4$R$_5$R$_6$ where R$_4$, R$_5$ and R$_6$ are independently hydrogen, methyl or ethyl; (f) N-pyridinium; (g) N'-3-methyl-N-1-imidazolium; or (h) NH—CR$_3$(=NH) where R$_3$ is hydrogen, methyl or amino;
and R$_7$ is selected from the group consisting of dichloromethyl, difluoromethyl, trifluoromethyl, cyanomethyl, azidomethyl, and aminomethyl;
provided that the sum of a+l+m+x is from 2 to 6; provided that if a is 1, then M is (CH$_2$)$_m$;
and provided that the group A$_a$L$_l$M$_m$X$_x$Y is other than an alpha-N-unfunctionalized glycine, ornithine or lysine residue;
and provided that when a is 0; one of more of L, M or X are CH$_2$; and Y is NH$_2$;
and pharmaceutically acceptable salts thereof.

3. A compound according to claim 2 in which Y is a positively charged moiety separated from the carbonyl group by at least two atoms in the chain.

4. A compound according to claim 2 in which a is zero.

5. A compound according to claim 1 in which a is 1.

6. A compound according to claim 2 in which L is CH$_2$ and l is an integer from 1 to 5.

7. A compound according to claim 2 in which M is CH$_2$ and m is an integer from 1 to 4.

8. A compound according to claim 2 in which X is CH$_2$ and x is an integer from 1 to 4.

9. A compound according to claim 2 in which Y is NR$_4$R$_5$R$_6$$^+$.

10. A compound according to claim 2 in which R$_7$ is dichloromethyl.

11. A pharmaceutical composition comprising a therapeutically effective amount of a compound or salt according to claim 1 and a pharmaceutically acceptable diluent or carrier.

12. A pharmaceutical composition comprising a therapeutically effective amount of a compound or salt according to claim 2 and a pharmaceutically acceptable diluent or carrier.

13. A pharmaceutical composition comprising a therapeutically effective amount of a compound or salt according to claim 10 and a pharmaceutically acceptable diluent or carrier.

14. A composition according to claim 11 further comprising an effective amount of one or more additional medicinal agents.

15. A composition according to claim 14 in which the one or more additional medicinal agents are selected from microbiocides, anthelmintics, ecto- and endoparasticides, antifluke agents, anti-inflammatories, anti-infectives, hormones, dermatological preparations, including antiseptics and disinfectants, and immunobiologicals including vaccines and antisera.

16. A method of treating a microbial infectious disease in a subject comprising administering to said subject a therapeutically effective amount of a compound according to claim 1.

17. A method of treating a microbial infectious disease in a subject comprising administering to said subject a therapeutically effective amount of a compound according to claim 2.

18. A method of treating a microbial infectious disease in a subject comprising administering to said subject a therapeutically effective amount of a composition according to claim 10.

19. A method of treating a microbial infectious disease in a subject comprising administering to said subject a therapeutically effective amount of a composition according to claim 13.

20. A method of treating a microbial infectious disease in a subject comprising administering to said subject a therapeutically effective amount of a composition according to claim 14.

21. A method of treating a microbial infectious disease in a subject comprising administering to said subject a therapeutically effective amount of a composition according to claim 15.

22. A compound having the Formula.

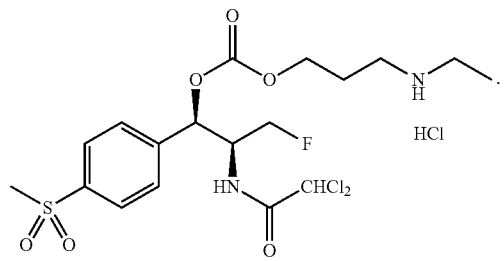

23. The compound of claim 2, wherein the sum of a+l+m+x is from 3 to 6.